(12) United States Patent
Xiao et al.

(10) Patent No.: US 9,796,739 B2
(45) Date of Patent: Oct. 24, 2017

(54) AZA-POLYSILANE PRECURSORS AND METHODS FOR DEPOSITING FILMS COMPRISING SAME

(71) Applicant: AIR PRODUCTS AND CHEMICALS, INC., Allentown, PA (US)

(72) Inventors: Manchao Xiao, San Diego, CA (US); Xinjian Lei, Vista, CA (US); Daniel P. Spence, Carlsbad, CA (US)

(73) Assignee: VERSUM MATERIALS US, LLC, Allentown, PA (US)

( * ) Notice: Subject to any disclaimer, the term of this patent is extended or adjusted under 35 U.S.C. 154(b) by 0 days.

(21) Appl. No.: 14/293,554

(22) Filed: Jun. 2, 2014

(65) Prior Publication Data
US 2015/0147871 A1     May 28, 2015

Related U.S. Application Data

(60) Provisional application No. 61/839,536, filed on Jun. 26, 2013.

(51) Int. Cl.
*C23C 16/34*     (2006.01)
*C07F 7/21*     (2006.01)
(Continued)

(52) U.S. Cl.
CPC .............. *C07F 7/21* (2013.01); *C07F 7/025* (2013.01); *C07F 7/10* (2013.01); *C23C 16/24* (2013.01);
(Continued)

(58) Field of Classification Search
None
See application file for complete search history.

(56) References Cited

U.S. PATENT DOCUMENTS

| 5,660,895 A | 8/1997 | Lee et al. |
| 7,019,159 B2 | 3/2006 | Dussarrat et al. |
| | (Continued) | |

FOREIGN PATENT DOCUMENTS

| CN | 1563016 | 1/2005 |
| EP | 1441042 | 7/2004 |
| | (Continued) | |

OTHER PUBLICATIONS

Schuh—Z anorg allg Chem 1993 v619 p. 1347.*
(Continued)

*Primary Examiner* — Joseph Miller, Jr.
(74) *Attorney, Agent, or Firm* — Anne B. Kiernan; Lina Yang

(57) ABSTRACT

Described herein are precursors and methods for forming silicon-containing films. In one aspect, there is provided an aza-polysilane precursor comprising at least two Si—N bonds, at least one Si—Si bond, and at least two $SiH_2$ groups represented by the following Formula IA, IB and IC:

IA (Continued)

-continued

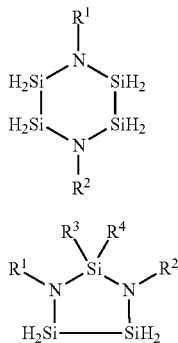

IB

IC wherein $R^1$ and $R^2$ are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, a $C_3$ to $C_{10}$ cyclic alkylamino group; wherein $R^1$ in Formula IA cannot both be methyl, $R^1$ and $R^2$ in Formula IB cannot both be iso-propyl, tert-butyl, and bezenyl and $R^3$ and $R^4$ cannot both be methyl and phenyl.

21 Claims, 1 Drawing Sheet

(51) Int. Cl.
*C07F 7/10* (2006.01)
*C23C 16/24* (2006.01)
*C23C 16/40* (2006.01)
*C23C 16/455* (2006.01)
*C07F 7/02* (2006.01)
*H01L 21/02* (2006.01)

(52) U.S. Cl.
CPC .......... *C23C 16/345* (2013.01); *C23C 16/401* (2013.01); *C23C 16/45544* (2013.01); *C23C 16/45553* (2013.01); *H01L 21/0217* (2013.01); *H01L 21/0228* (2013.01); *H01L 21/0262* (2013.01); *H01L 21/02126* (2013.01); *H01L 21/02164* (2013.01); *H01L 21/02167* (2013.01); *H01L 21/02274* (2013.01); *H01L 21/02532* (2013.01); *H01L 21/02592* (2013.01)

(56) References Cited

U.S. PATENT DOCUMENTS

| | | | |
|---|---|---|---|
| 7,064,083 B2 | 6/2006 | Dussarrat et al. | |
| 7,077,904 B2 | 7/2006 | Cho et al. | |
| 7,446,217 B2 | 11/2008 | Wang et al. | |
| 7,531,679 B2 | 5/2009 | Wang et al. | |
| 7,713,346 B2 | 5/2010 | Wang et al. | |
| 7,786,320 B2 | 8/2010 | Wang et al. | |
| 7,887,883 B2 | 2/2011 | Wang et al. | |
| 7,910,765 B2 | 3/2011 | Wang et al. | |
| 8,153,832 B2 | 4/2012 | Dussarrat | |
| 2002/0175393 A1* | 11/2002 | Baum | C07F 7/006 257/506 |
| 2004/0096582 A1* | 5/2004 | Wang | C07F 7/025 427/255.27 |
| 2005/0080285 A1 | 4/2005 | Wang et al. | |
| 2005/0118837 A1* | 6/2005 | Todd | C23C 16/24 438/791 |
| 2006/0258173 A1 | 11/2006 | Xiao et al. | |
| 2009/0209081 A1 | 8/2009 | Matero et al. | |
| 2010/0041243 A1* | 2/2010 | Cheng | C23C 16/345 438/778 |
| 2011/0301373 A1 | 12/2011 | Knies et al. | |
| 2013/0078392 A1 | 3/2013 | Xiao et al. | |
| 2013/0109155 A1 | 5/2013 | Okada et al. | |
| 2013/0123528 A1 | 5/2013 | Tada et al. | |
| 2014/0287164 A1 | 9/2014 | Xiao et al. | |

FOREIGN PATENT DOCUMENTS

| | | |
|---|---|---|
| JP | 2007051363 | 1/2007 |
| JP | 2007508307 | 4/2007 |
| JP | 2012126704 | 5/2012 |
| JP | 2012518666 | 8/2012 |
| JP | 2013100262 | 5/2013 |
| TW | 201250046 | 12/2012 |
| WO | 2005038871 | 4/2005 |
| WO | 2007112779 | 10/2007 |
| WO | 2010097303 | 9/2010 |
| WO | WO2011005653 | * 1/2011 |

OTHER PUBLICATIONS

Soeldner—Inorg Chem 1997 v36 p. 1758-63.*
Schuh, H., T. Schlosser, P. Bissinger and H. Schmidbaur (1993). "Disilanylamines. Compounds comprising the structural unit silicon-silicon-nitrogen, as single-source precursors for plasma-enhanced chemical vapor deposition (PE-CVD) of silicon nitride." Z. Anorg. Allg. Chem. FIELD Full Journal Title:Zeitschrift fuer Anorganische und Allgemeine Chemie 619(8): 1347-52.
Soeldner, M., A. Schier and H. Schmidbaur (1997). "1,2-Disilanediyl Bis(triflate), F3CSO3—SiH2SiH2—O3SCF3, as the Key Intermediate for a Facile Preparation of Open-Chain and Cyclic 1,1- and 1,2-Diaminodisilanes." Inorg. Chem. FIELD Full Journal Title:Inorganic Chemistry 36(9): 1758-1763.
Abedini, M. and MacDiarmid, A., "The Preparation and Properties of Some New Nitrogen and Fluorine Derivatives of Disilane", Inorganic Chemistry, 1962, 608-613.
Soeldner, et al, "Binary Si/N-[4.4]-Spirocycles with Two SiH2SiH2 Loops", Inorganic Chemistry, 1998, 510-515.
Soeldner, et al, "Isomeric Cyclic Disilanediyl Dimethylhydrazines", Inorganic Chemistry, 1998, 601-603.
Yoshioka, et al, "Nuclear magnetic resonance coupling constant relationships in analogous ethyl, disilanyl, silymethyl, and methylsilyl compounds", Journal of Molecular Spectroscopy, 1966, 103-106.
Charles H. Van Dyke, et al, "The Proton Nuclear Magnetic Resonance Spectra of Silicon Analogs of Simple Ethyl Compounds", Inorganic Chemistry, 1964, 1071-1077.

* cited by examiner

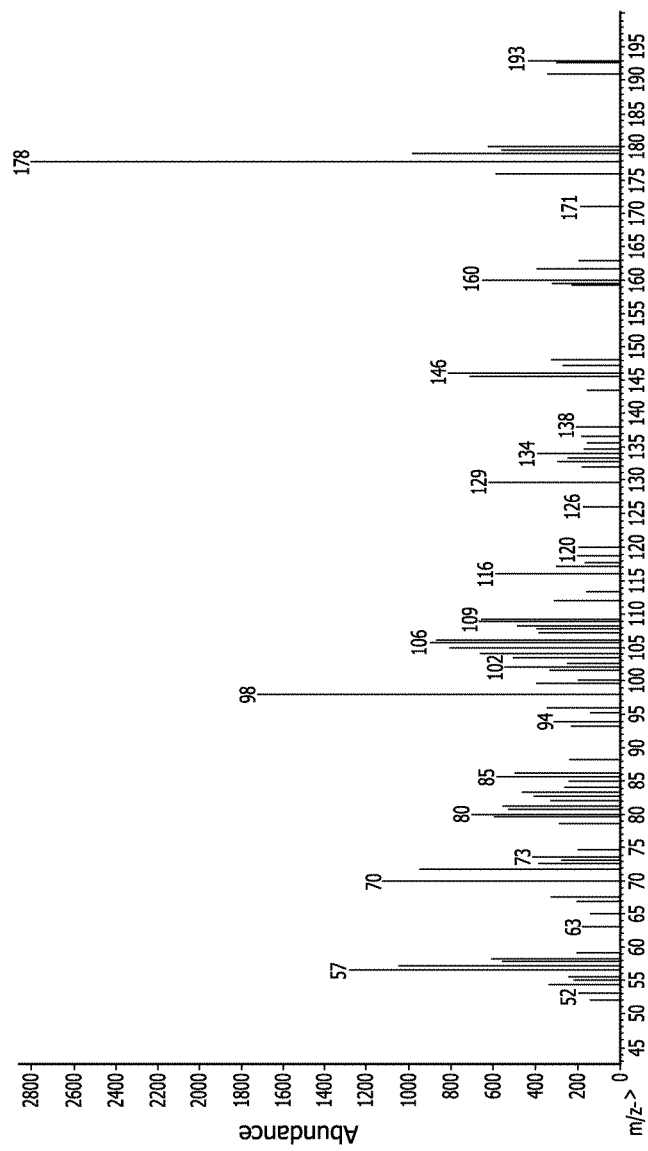

AZA-POLYSILANE PRECURSORS AND METHODS FOR DEPOSITING FILMS COMPRISING SAME

CROSS REFERENCE TO RELATED APPLICATIONS

This application claims the benefit of U.S. Provisional Application No. 61/839,536, filed Jun. 26, 2013, which is hereby incorporated by reference as if fully set forth.

BACKGROUND OF THE INVENTION

Precursors, particularly silicon-containing compounds, and compositions thereof that can be used for the deposition of silicon-containing films, including but not limited to, silicon amorphous silicon, crystalline silicon, silicon nitride, silicon oxide, carbon doped silicon oxide, silicon carbonitride, and silicon oxynitride films are described herein. In yet another aspect, described herein is the use of the aza-polysilane precursors for depositing silicon-containing films in the fabrication of integrated circuit devices. In these or other aspects, the aza-polysilane precursors may be used for a variety of deposition processes, including but not limited to, atomic layer deposition ("ALD"), chemical vapor deposition ("CVD"), plasma enhanced chemical vapor deposition ("PECVD"), low pressure chemical vapor deposition ("LPCVD"), and atmospheric pressure chemical vapor deposition.

Several classes of silicon-containing compounds can be used as precursors for silicon-containing films such as, but not limited to, silicon oxide, carbon doped silicon oxide or silicon nitride films. Examples of these compounds suitable for use as precursors include silanes, disilanes, chlorosilanes, polysilazanes, aminosilanes, and azidosilanes. Inert carrier gas or diluents such as, but not limited, helium, hydrogen, nitrogen, etc., are also used to deliver the precursors to the reaction chamber.

Low pressure chemical vapor deposition (LPCVD) processes are one of the more widely accepted methods used by semiconductor industry for the deposition of silicon-containing films. Low pressure chemical vapor deposition (LP-CVD) using ammonia may require deposition temperatures of greater than 750° C. to obtain reasonable growth rates and uniformities. Higher deposition temperatures are typically employed to provide improved film properties. One of the more common industry methods to grow silicon nitride or other silicon-containing films is through low pressure chemical vapor deposition in a hot wall reactor at temperatures >750° C. using the precursors silane, dichlorosilane, and/or ammonia. However, there are several drawbacks using this method. For example, certain precursors, such as silane are pyrophoric. This may present problems in handling and usage. Also, films deposited from silane and dichlorosilane may contain certain impurities. For example, films deposited using dichlorosilane may contain certain impurities, such as chlorine and ammonium chloride, which are formed as byproducts during the deposition process. Films deposited using silane may contain hydrogen.

Precursors that are used in depositing silicon nitride films such as BTBAS and chlorosilanes generally deposit the films at temperatures greater than 550° C. The trend of miniaturization of semiconductor devices and low thermal budget requires lower process temperature and higher deposition rate. The temperature, at which the silicon films are deposited, should decrease in order to prevent ion diffusion in the lattice, particularly for those substrates comprising metallization layers and on many Group III-V and II-VI devices. Accordingly, there is a need in the art to provide precursors for the deposition of silicon-containing films, such as silicon oxide, carbon doped silicon oxide, silicon oxynitride, or silicon nitride films that are sufficiently chemically reactive to allow deposition via CVD, ALD or other processes at temperatures of 550° C. or below or even at room temperature.

The reference entitled "Disilanyl-amines—Compounds Comprising the Structure Unit Si—Si—N, as Single-Source Precursors for Plasma-Enhanced Chemical Vapor Deposition (PE-CVD) of Silicon Nitride", Schuh et al., Zeitschrift Für Anorganische and Allgemeine Chemie, 619 (1993), pp. 1347-52 describes potential single-source precursors for PECVD of silicon nitride films wherein the precursors have the structural unit Si—Si—N such as $(Et_2N)_2HSi$—$SiH_3$, $(Et_2N)_2HSi$—$SiH(Net_2)_2$, $[(i-Pr)_2N]H_2Si$—$SiH_3$ and $[(i-Pr)_2 N]H_2Si$—$SiH_2[N(i-Pr)_2]$. The precursor 1,2-bis(di-isopropylamino)disilane (BIPADS) was used for the PECVD deposition of silicon nitride films. The resulting films from the BIPADS precursor exhibited refractive indices ranging from 1.631-1.814 and had low carbon and very low oxygen contents but high (Si-bound) hydrogen contents.

The reference entitled "1,2-Disilanediyl Bis(triflate), $F_3CSO_3$—$SiH_2$—$SiH_2$—$O_3SCF_3$, as the Key Intermediate for a Facile Preparation of Open-Chain and Cyclic 1,1- and 1,2-Diaminodisilanes", Sölder et al., Inorganic Chemistry, 36 (1997), pp. 1758-63 describes high yield syntheses for several open-chain and cyclic diaminodisilanes with fully hydrogenated Si linkages.

The reference titled "Proton magnetic resonance spectra and base strengths of disilanylamines." Abedini et al., Quarterly Bulletin of the Faculty of Science, Tehran University 3(4): 1-6 discloses PMR spectra of disilanylamines suggested that their basicities decreased in the order: $Me_3N > H_3SiSiH_2NMe_2 > (H_3SiSiH_2)_2NMe > (H_3SiSiH_2)_3N$.

U.S. Pat. No. 5,660,895 describes the deposition of high-quality $SiO_2$ films at low temperatures in a PECVD process using disilane ($Si_2H_6$) and nitrous oxide.

U.S. Pat. Nos. 7,019,159 and 7,064,083 describe a composition and method of preparing silane compounds or hexakis(monohydrocarbylamino)disilanes that are free of chlorine and have the formula: $((R)HN)_3$—Si—Si—$(NH(R))_3$ wherein R independently represents a $C_1$ to $C_4$ hydrocarbyl. The hexakis(monohydrocarbylamino)disilane precursors are used for the deposition of silicon nitride or silicon oxynitride films.

U.S. Pat. No. 8,153,832 describes pentakis(dimethylamino)disilane compounds having the formula: $Si_2(NMe_2)_5Y$ where Y is selected from the group consisting of H, Cl, or an amino group and its use for manufacturing gate silicon-containing films or etch-stop silicon-containing films of SiN or SiON.

US Publ. No. 2009/0209081 A describes methods for depositing silicon dioxide containing thin films on a substrate using hexakis(monoalkylamino)disilane such as hexakis(ethylamino)disilane as silicon source and ozone as oxidant. The growth rate was about 1.1 Å/cycle.

U.S. Pat. No. 7,077,904 describes methods for depositing silicon dioxide containing thin films on a substrate using hexachlorodisilane as silicon source and water as oxidant in presence of catalyst such as pyridine. The growth rates were in the range from 2.6 to 0.6 Å/cycle at substrate temperatures from 50 to 140° C.

US Publ. No. 2013/0109155 describes a method of forming a seed layer for a thin film using an aminosilane based gas having two Si atoms such as hexakisethylaminodisilane ($C_{12}H_{36}N_6Si_2$). Other aminosilanes having the following formulas may also be used: (1) (R1R2)N)nSi2H6-n-m (R3)m . . . n: the number of amino groups, m: the number of alkyl groups or (2) (R1)NH)nSi2H6-n-m(R3)m . . . n: the number of amino groups, m: the number of alkyl groups. In formulas (1) and (2), R1, R2, R3=$CH_3$, $C_2H_5$, $C_3H_7$, R1=R2=R3 or may not be the same as each other, n=an integer ranging from 1 to 6 and m=0, and 1 to 5.

U.S. Pat. Nos. 7,446,217; 7,531,679; 7,713,346; 7,786,320; 7,887,883; and 7,910,765 describe silane precursors that comprise at least one disilane derivative that is fully substituted with alkylamino and/or dialkylamino functional groups.

BRIEF SUMMARY OF THE INVENTION

Described herein are aza-polysilane precursors, having one or more of the following: a Si—N bond, a Si—Si bond, a $SiH_2$ group, and combinations thereof, more specifically at least two Si—N bonds, at least one Si—Si bond, and at least two $SiH_2$ groups, compositions comprising same, and methods using same for forming films comprising silicon, such as, but not limited to, amorphous silicon, crystalline silicon, silicon oxide, carbon doped silicon oxide, silicon nitride, silicon oxynitride, silicon carbide, silicon carbonitride, and combinations thereof onto at least a portion of a substrate. In addition, described herein is a composition comprising an aza-polysilane described herein wherein the aza-polysilane is substantially free of at least one selected from the amines, halides, higher molecular weight species, and trace metals. In these or other embodiments, the composition may further comprise a solvent. Also disclosed herein are the methods to form films comprising silicon or coatings on an object to be processed, such as, for example, a semiconductor wafer. In one embodiment of the method described herein, a film comprising silicon and oxygen is deposited onto a substrate using an aza-polysilane precursor and an oxygen-containing source in a deposition chamber under conditions for generating a silicon oxide or a carbon doped silicon oxide film on the substrate. In another embodiment of the method described herein, a film comprising silicon and nitrogen is deposited onto a substrate using an aza-polysilane precursor and a nitrogen containing precursor in a deposition chamber under conditions for generating a silicon nitride film on the substrate. In a further embodiment, the aza-polysilane precursor described herein can also be used a dopant for metal containing films, such as but not limited to, metal oxide films or metal nitride films. In the compositions and methods described herein, an aza-polysilane having the formula described herein is employed as at least one of the silicon containing precursors.

In one aspect, the aza-polysilane precursor described herein is represented by the following Formulae IA, IB and IC and comprises at least two Si—N bonds, at least one Si—Si bond, and an at least two $SiH_2$ groups:

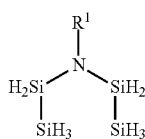

IA

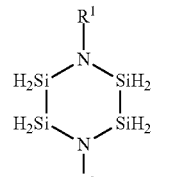

IB

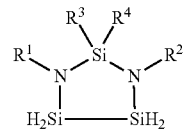

IC wherein $R^1$ and $R^2$ are each independently selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, a $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; wherein $R^1$ in Formula IA cannot both be methyl, $R^1$ and $R^2$ in Formula IB cannot both be iso-propyl, tert-butyl, and bezenyl and $R^3$ and $R^4$ cannot both be methyl and phenyl in formula IC.

In another aspect, there is provided a composition comprising: (a) at least one aza-polysilane precursor comprising at least two Si—N bonds, at least one Si—Si bond, and at least two $SiH_2$ groups and represented by the following Formulae IA, IB, and IC:

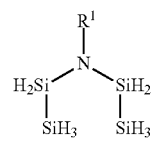

IA

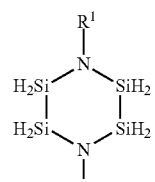

IB

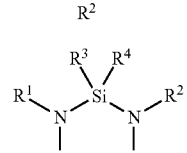

IC wherein $R^1$ and $R^2$ are each independently selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, a $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group; (b) a solvent has a boiling point and a difference between the boiling point of the solvent and a boiling point of the at least one aza-polysilane is 40° C. or less. With regard to the latter, the difference in boiling points between the aza-polysilane and the solvent is 40° C. or less, 20° C. or less, or 10° C. or less. In certain embodiments, the solvent in the composition includes, but is not limited to, ether, tertiary amine, alkyl hydrocarbon, aromatic hydrocarbon, and tertiary aminoether.

In another aspect, there is provided a method for forming a silicon-containing film on at least one surface of a substrate comprising:

providing the at least one surface of the substrate in a reaction chamber; and forming the silicon-containing film on the at least one surface by a deposition process chosen from a chemical vapor deposition process and an atomic layer deposition process using at least an aza-polysilane precursor comprising at least two Si—N bonds, at least one Si—Si bond, and at least two SiH$_2$ groups represented by the following Formulae IA, IB, IC:

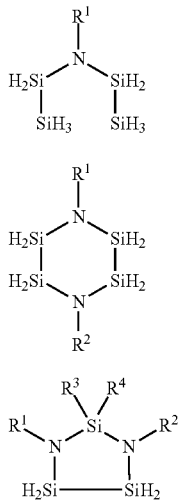

wherein $R^1$ and $R^2$ are each independently selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, a $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group.

In another aspect, there is provided a method for forming a silicon-containing film on at least one surface of a substrate comprising:

providing the at least one surface of the substrate in a reaction chamber; and forming the silicon-containing film on the at least one surface by a deposition process chosen from a chemical vapor deposition process and an atomic layer deposition process using at least an aza-polysilane precursor comprising at least two Si—N bonds, at least one Si—Si bond, and at least two SiH$_2$ groups represented by the following Formulae IA, IB, IC:

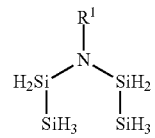

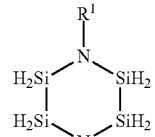

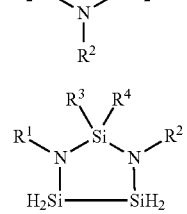

wherein $R^1$ and $R^2$ are each independently selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, a $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group.

In another aspect, there is provided a method of forming a silicon oxide film or a carbon doped silicon oxide film via an atomic layer deposition process or ALD-like process, the method comprising the steps of:

a. providing a substrate in a reactor;
b. introducing into the reactor at least one aza-polysilane precursor comprising at least two Si—N bonds, at least one Si—Si bond, and at least two SiH$_2$ groups represented by the following Formulae IA, IB, IC:

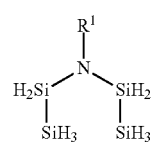

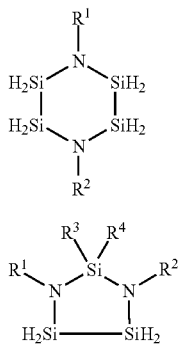

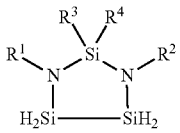

wherein $R^1$ and $R^2$ are each independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group;

c. purging the reactor with a purge gas;

d. introducing an oxygen-containing source into the reactor; and e. purging the reactor with a purge gas; wherein steps b through e are repeated until a desired thickness of the film is obtained. In certain embodiments, $R^1$ and $R^2$ in Formula IB are the same. In other embodiments, $R^1$ and $R^2$ in Formula IB are different.

In a further aspect, there is provided a method of forming a film selected from a silicon oxide film and a carbon doped silicon oxide film onto at least a surface of a substrate using a CVD process comprising:

a. providing a substrate in a reactor;

b. introducing into the reactor at least one aza-polysilane precursor comprising at least two Si—N bonds, at least one Si—Si bond, and at least two SiH$_2$ groups represented by the following Formulae IA, IB, IC:

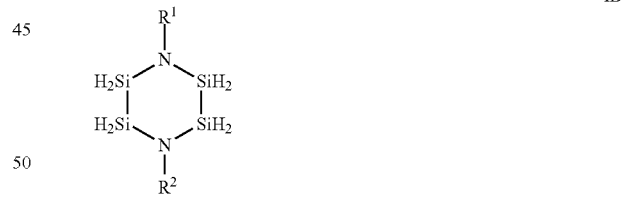

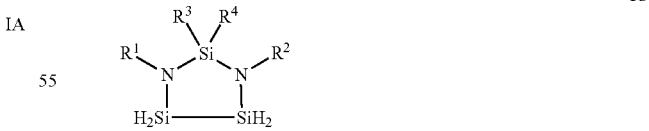

wherein $R^1$ and $R^2$ are each independently selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, a $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group; and c. providing an oxygen-containing source to deposit the film onto the at least one surface. In certain embodiments of the method, $R^1$ and $R^2$ in Formula IB are the same. In other embodiments, $R^1$ and $R^2$ in Formula IB are different.

In another aspect, there is provided a method of forming a silicon nitride film via an atomic layer deposition process, the method comprising the steps of:

a. providing a substrate in a reactor;

b. introducing into the reactor an at least one aza-polysilane precursor comprising at least two Si—N bonds, at least one Si—Si bond, and at least two SiH$_2$ groups represented by the following Formula IA, IB, IC:

or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group;

c. purging the reactor with a purge gas;

d. introducing a nitrogen-containing source into the reactor;

e. purging the reactor with a purge gas; and wherein steps b through e are repeated until a desired thickness of the silicon nitride film is obtained. In certain embodiments, $R^1$ and $R^2$ in Formula IB are the same. In other embodiments, $R^1$ and $R^2$ in Formula IB are different.

In a further aspect, there is provided a method of forming a silicon nitride film onto at least a surface of a substrate using a CVD process comprising:

a. providing a substrate in a reactor;

b. introducing into the reactor at least one aza-polysilane precursor comprising at least two Si—N bonds, at least one Si—Si bond, and at least two $SiH_2$ groups represented by the following Formulae IA, IB, IC:

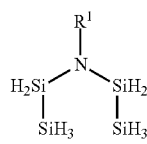

IA

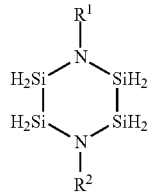

IB

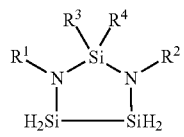

IC wherein $R^1$ and $R^2$ are each independently selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, a $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group;

c. providing a nitrogen-containing source wherein the at least one aza-polysilane precursors and the nitrogen-containing source react to deposit the film onto the at least one surface. In certain embodiments, $R^1$ and $R^2$ of Formula IB are the same. In other embodiments, $R^1$ and $R^2$ of Formula IB are different.

In a further embodiment of the method described herein, the process is depositing an amorphous or a crystalline silicon film. In this embodiment, the method comprises:

placing one or more substrates into a reactor which is heated to one or more temperatures ranging from ambient temperature to about 700° C.;

introducing at least one aza-polysilane precursor comprising at least two Si—N bonds, at least one Si—Si bond, and at least two $SiH_2$ groups represented by the following Formulae IA, IB, IC:

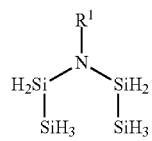

IA

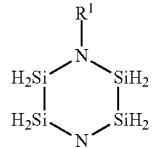

IB

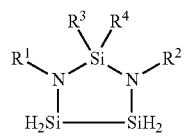

IC wherein $R^1$ and $R^2$ are each independently selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, a $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group; and providing a reducing agent source into the reactor to at least partially react with the at least one aza-polysilane precursor and deposit a silicon-containing film onto the one or more substrates. The reducing agent is selected from the group consisting of hydrogen, hydrogen plasma, and hydrogen chloride. In certain embodiments of the CVD method, the reactor is maintained at a pressure ranging from 10 mTorr to 760 Torr during the introducing step. The above steps define one cycle for the method described herein, and the cycle of steps can be repeated until the desired thickness of a film is obtained. In certain embodiments, $R^1$ and $R^2$ of Formula IB are the same. In other embodiments, $R^1$ and $R^2$ of Formula IB are different.

In another aspect, there is provided a method of depositing an amorphous or a crystalline silicon film via an atomic layer deposition or cyclic chemical vapor deposition process, the method comprising the steps of:

a. providing a substrate in a reactor;

b. introducing into the reactor at least one aza-polysilane precursor comprising at least two Si—N bonds, at least one Si—Si bond, and at least two $SiH_2$ groups represented by the following Formulae IA, IB, IC:

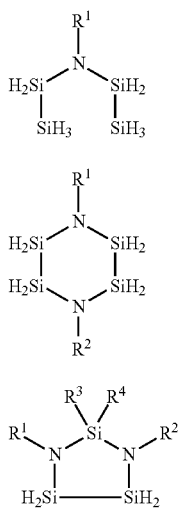

wherein $R^1$ and $R^2$ are each independently selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, a $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_6$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_6$ cyclic alkylamino group wherein step b is repeated until a desired thickness of the film is obtained. In certain embodiments, the thickness of the film can be 1 Å or greater, or 1 to 10,000 Å, or 1 to 1000 Å, or 1 to 100 Å.

In another aspect, a vessel for depositing a silicon-containing film comprising one or more aza-polysilane precursor having Formulae IA, IB, and IC is described herein. In one particular embodiment, the vessel comprises at least one pressurizable vessel (preferably of stainless steel) fitted with the proper valves and fittings to allow the delivery of one or more precursors to the reactor for a CVD or an ALD process.

BRIEF DESCRIPTION OF SEVERAL VIEWS OF THE DRAWINGS

FIG. 1 provides the Mass Spectrometry (MS) of 3-tert-butyl-3-aza-pentasilane.

DETAILED DESCRIPTION OF THE INVENTION

The aza-polysilane(s) described herein are used as precursors to form stoichiometric and non-stoichiometric silicon containing films such as, but not limited to, amorphous silicon, crystalline silicon, silicon oxide, silicon oxycarbide, silicon nitride, silicon oxynitride, and silicon oxycarbonitride. These precursors can also be used, for example, as dopants for metal containing films. The aza-polysilane precursors used in semi-conductor processes are typically high purity volatile liquid precursor chemical that are vaporized and delivered to a deposition chamber or reactor as a gas to deposit a silicon containing film via CVD or ALD processes for semiconductor devices. The selection of precursor materials for deposition depends upon the desired resultant silicon-containing material or film. For example, a precursor material may be chosen for its content of chemical elements, its stoichiometric ratios of the chemical elements, and/or the resultant silicon containing film or coating that are formed under CVD. The precursor material may also be chosen for various other characteristics such as cost, relatively low toxicity, handling characteristics, ability to maintain liquid phase at room temperature, volatility, molecular weight, and/or other considerations. In certain embodiments, the precursors described herein can be delivered to the reactor system by any number of means, preferably using a pressurizable stainless steel vessel fitted with the proper valves and fittings, to allow the delivery of liquid phase precursor to the deposition chamber or reactor.

The aza-polysilane precursors described herein exhibit a balance of reactivity and stability that makes them ideally suitable as CVD or ALD precursors in microelectronic device manufacturing processes. With regard to reactivity, certain precursors may have boiling points that are too high to be vaporized and delivered to the reactor to be deposited as a film on a substrate. Precursors having higher relative boiling points require that the delivery container and lines need to be heated at or above the boiling point of the precursor under a given vacuum to prevent condensation or particles from forming in the container, lines, or both. With regard to stability, other precursors may form silane ($SiH_4$) or disilane ($Si_2H_6$) as they degrade. Silane is pyrophoric at room temperature or it can spontaneously combust which presents safety and handling issues. Moreover, the formation of silane or disilane and other by-products decreases the purity level of the precursor and changes as small as 1-2% in chemical purity may be considered unacceptable for reliable semiconductor manufacture. In certain embodiments, the aza-polysilane precursors having Formulae IA, IB, and IC described herein comprise 2% or less by weight, or 1% or less by weight, or 0.5% or less by weight of by-product (such as the corresponding bis-disilane byproduct) after being stored for a time period of 6 months or greater, or one year or greater which is indicative of being shelf stable. In addition to the foregoing advantages, in certain embodiments, such as for depositing a silicon oxide or silicon nitride or silicon film using an ALD, ALD-like, PEALD, or CCVD deposition method, the aza-polysilane precursor described herein may be able to deposit high density materials at relatively low deposition temperatures, e.g., 500° C. or less, or 400° C. or less, 300° C. or less, 200° C. or less, 100° C. or less, or 50° C. or less. In one particular embodiment, the aza-polysilane precursor, such as 3-isopropyl-3-aza-pentasilane, 3-tert-butyl-3-aza-pentasilane, 3-tert-pentyl-3-aza-pentasilane, 3-cyclopentyl-3-aza-pentasilane, 3-cyclohexyl-3-aza-pentasilane, 3-(2,6-dim ethylcyclohexyl-3-aza-pentasilane, 3-(tetrahydropyran-4-yl)-3-aza-pentasilane, 3-(1-methylpiperidin-4-yl)-3-aza-pentasilane, 3-phenyl-3-aza-pentasilane, 3-(2-methyl-tolyl)-3-aza-pentasilane, 3-(2,6-dimethyl-tolyl)-3-aza-pentasilane, 3-(pyridin-3-yl)-3-aza-pentasilane, 3-(4-methylpyridin-3-yl)-3-aza-pentasilane 1,4-bis(cyclopentyl)-1,4-diaza-2,3,5,6-tetrasilacyclohexane, 1,4-bis(cyclohexyl)-1,4-diaza-2,3,5,6-tetrasilacyclohexane, 1,4-bis(2,6-dimethylcyclohexyl)-1,4-Diaza-2,3,5,6-tetrasilacyclohexane, 1,4-bis(iso-propyl)-1,4-diaza-2,3,5,6-tetrasilacyclohexane, 1,4-bis(tert-butyl)-1,4-diaza-2,3,5,6-tetrasilacyclohexane, 1,4-bis(tert-pentyl)-1,4-diaza-2,3,5,6-tetrasilacyclohexane, 2,4-bis(isopropyl)- diaza-1,3,5-trisilacyclopentane, 2,4-bis(tert-butyl)-diaza-1,3,5-trisilacyclopentane, 2,4-bis(tert-butyl)-diaza-1,3,5-trisilacyclopentane can be used to deposit a silicon-containing film via ALD or PEALD at a temperature as low as 50° C. or less or at ambient or room temperature (e.g., 25° C.).

In one embodiment, described herein is a composition for forming a silicon-containing film comprising: an aza-polysilane having Formulae IA, IB, and IC described herein and a solvent(s). Without being bound by any theory, it is believed that composition described herein may provide one or more advantages compared to pure organoaminosilane or hexachlorodisilane. These advantages include: better usage of the aza-polysilane in semiconductor processes, better stability over long term storage, cleaner evaporation by flash vaporization, and/or overall more stable direct liquid injection (DLI) chemical vapor deposition process. The weight percentage of the aza-polysilane in the composition can range from 1 to 99% with the balance being solvent(s) wherein the solvent(s) does not react with the aza-polysilane and has a boiling point similar to the aza-polysilane. With regard to the latter, the difference between the boiling points of the aza-polysilane and solvent(s) in the composition is 40° C. or less, more preferably 20° C. or less, or 10° C. or less. Exemplary compositions include, but not limited to, a mixture of di-iso-3-tert-butyl-3-aza-pentasilane (b.p. about 150° C.) and octane (b.p. 125 to 126° C.), a mixture of di-iso-3-tert-butyl-3-aza-pentasilane (b.p. about 150° C.) and ethylcyclohexane (b.p. 130-132° C.), 1,4-bis(tert-butyl)-1,4-diaza-2,3,5,6-tetrasilacyclohexane (b.p. about 200° C. and 2,2'-oxybis(N,N-dimethylethanamine (b.p., 189° C.).

In one aspect, the precursor described herein comprises at least one aza-polysilane precursor comprising at least two Si—N bonds, at least one Si—Si bond, and at least two $SiH_2$ groups represented by the following Formulae IA, IB, and IC:

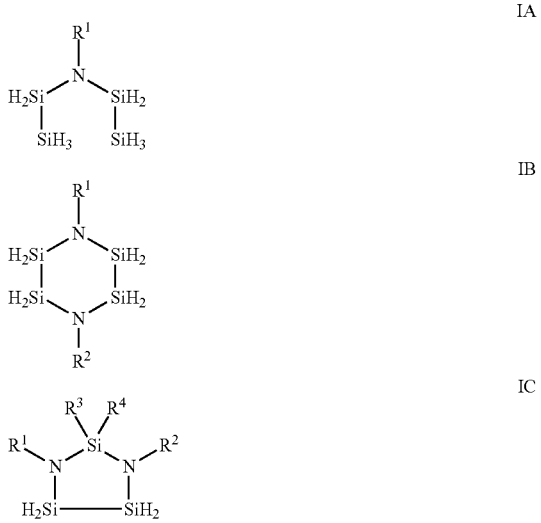

wherein $R^1$ and $R^2$ are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, a $C_3$ to $C_6$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, a $C_3$ to $C_6$ cyclic alkylamino group; wherein $R^1$ in Formula IA cannot both be methyl, $R^1$ and $R^2$ in Formula IB cannot both be iso-propyl, tert-butyl, and bezenyl and $R^3$ and $R^4$ cannot both be methyl and phenyl.

In another aspect, there is provided a composition comprising: (a) at least one aza-polysilane precursor comprising at least two Si—N bonds, at least one Si—Si bond, and at least two $SiH_2$ groups represented by the following Formulae IA, IB, IC:

wherein $R^1$ and $R^2$ are each independently selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_3$ to $C_{10}$ cyclic alkyl group, a $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_6$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_6$ cyclic alkylamino group; and (b) a solvent having a boiling point wherein the difference between the boiling point of the solvent and the at least one aza-polysilane is 40° C. or less, or 120° C. or less, or 10° C. or less. Exemplary solvents include, but not limited to, ether, tertiary amine, alkyl hydrocarbon, aromatic hydrocarbon, tertiary aminoether.

In another aspect, there is provided a method for forming a silicon-containing film on at least one surface of a substrate comprising:

providing the at least one surface of the substrate in a reaction chamber; and forming the silicon-containing film on the at least one surface by a deposition process chosen from a chemical vapor deposition process and an atomic layer deposition process using at least an aza-polysilane precursor comprising at least two Si—N bonds, at least one Si—Si bond, and at least two SiH$_2$ groups represented by the following Formulae IA, IB, IC:

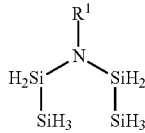

IA

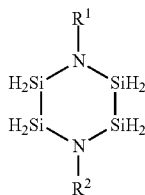

IB

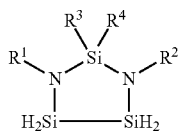

IC wherein R$^1$ and R$^2$ are each independently selected from a linear or branched C$_1$ to C$_{10}$ alkyl group, a linear or branched C$_3$ to C$_{10}$ alkenyl group, a linear or branched C$_3$ to C$_{10}$ alkynyl group, a C$_3$ to C$_{10}$ cyclic alkyl group, a C$_3$ to C$_{10}$ hetero-cyclic alkyl group, a C$_5$ to C$_{10}$ aryl group, a C$_3$ to C$_{10}$ hetero-aryl group, a C$_2$ to C$_{10}$ dialkylamino group, and a C$_3$ to C$_6$ cyclic alkylamino group; R$^3$ and R$^4$ are independently selected from hydrogen, a linear or branched C$_1$ to C$_{10}$ alkyl group, a linear or branched C$_2$ to C$_{10}$ alkenyl group, a linear or branched C$_2$ to C$_{10}$ alkynyl group, C$_3$ to C$_{10}$ cyclic alkyl group, C$_3$ to C$_{10}$ hetero-cyclic alkyl group, a C$_5$ to C$_{10}$ aryl group, and a C$_3$ to C$_{10}$ hetero-aryl group, a C$_2$ to C$_{10}$ dialkylamino group, and a C$_3$ to C$_{10}$ cyclic alkylamino group.

In the formulae herein and throughout the description, the term "alkyl" denotes a hydrocarbon group having from 1 to 10 or from 4 to 10 carbon atoms or from 5 to 10 carbon atoms. Exemplary alkyl groups include, but are not limited to, methyl, ethyl, n-propul, iso-propyl, n-butyl, sec-butyl, iso-butyl, tert-butyl, tert-pentyl groups. Exemplary aza-polysilanes having alkyl groups for R$^1$ in Formula IA and R$^1$ and R$^2$ in Formula IB include, but are not limited to:

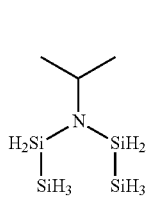 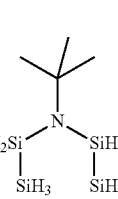 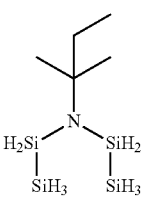

3-iso-propyl-3-aza-pentasilane | 3-tert-butyl-3-aza-pentasilane | 3-tert-pentyl-3-aza-pentasilane

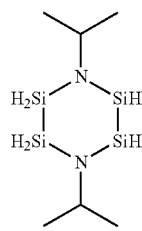 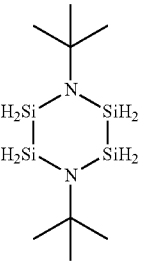 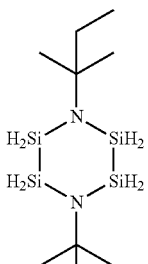

1,4-bis(iso-propyl)-1,4-diaza-2,3,5,6-tetrasilacyclohexane | 1,4-bis(tert-butyl)-1,4-diaza-2,3,5,6-tetrasilacyclohexane | 1,4-bis(tert-pentyl)-1,4-diaza-2,3,5,6-tetrasilacyclohexane In the formulae and throughout the description, the term "cyclic alkyl" denotes a cyclic functional group having from 3 to 10 or from 4 to 10 carbon atoms or from 5 to 10 carbon atoms. Exemplary cyclic alkyl groups include, but are not limited to, cyclobutyl, cyclopentyl, cyclohexyl, and cyclooctyl groups. Exemplary aza-polysilanes having cyclic alkyl groups for R$^1$ in Formula IA and R$^1$ and R$^2$ in Formula IB include, but are not limited to:

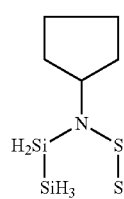 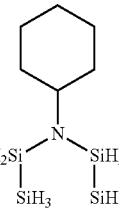 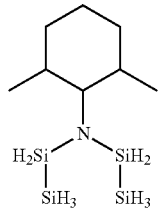

3-cyclopentyl-3-aza-pentasilane | 3-cyclohexyl-3-aza-pentasilane | 3-(2,6-dimethylcyclohexyl-3-aza-pentasilane

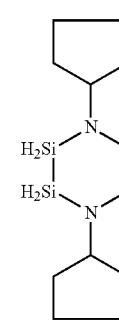 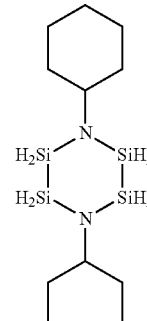 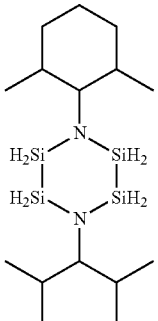

1,4-bis(cyclopentyl)-1,4-diaza-2,3,5,6-tetrasilacyclohexane | 1,4-bis(cyclohexyl)-1,4-diaza-2,3,5,6-tetrasilacyclohexane | 1,4-bis(2,6-dimethylcyclohexyl)-1,4-diaza-2,3,5,6-tetrasilacyclohexane In the formulae and throughout the description, the term "hetero-cyclic alkyl" denotes a cyclic functional group having from 3 to 10 or from 4 to 10 carbon atoms or from 5 to 10 carbon atoms as well as at least one oxygen atom or nitrogen atom or both. Exemplary aza-polysilanes having hetero-cyclic alkyl groups include, but are not limited to:

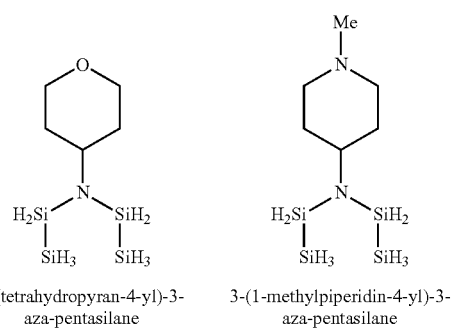

3-(tetrahydropyran-4-yl)-3-aza-pentasilane 3-(1-methylpiperidin-4-yl)-3-aza-pentasilane In the formulae and throughout the description, the term "aryl" denotes an aromatic cyclic functional group having from 5 to 12 carbon atoms or from 6 to 10 carbon atoms. Exemplary aryl groups include, but are not limited to, phenyl, benzyl, chlorobenzyl, tolyl, and o-xylyl. Exemplary aza-polysilanes having aryl groups include, but are not limited to:

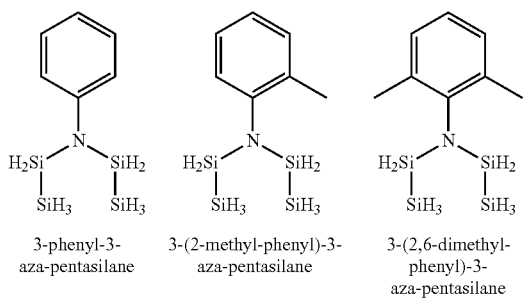

3-phenyl-3-aza-pentasilane 3-(2-methyl-phenyl)-3-aza-pentasilane 3-(2,6-dimethyl-phenyl)-3-aza-pentasilane In the formulae and throughout the description, the term "hetero-aryl" denotes an aromatic cyclic functional group having from 3 to 12 carbon atoms or from 3 to 10 carbon atoms as well as at least one oxygen atom or nitrogen atom or both. Exemplary aza-polysilanes having hetero-aryl groups for $R^1$ in Formula IA include, but are not limited to:

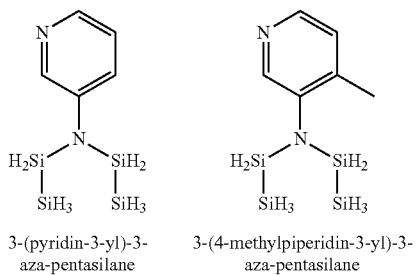

3-(pyridin-3-yl)-3-aza-pentasilane 3-(4-methylpiperidin-3-yl)-3-aza-pentasilane

In the formulae and throughout the description, the term "alkenyl group" denotes a group which has one or more carbon-carbon double bonds and has from 3 to 10 or from 3 to 6 or from 3 to 4 carbon atoms.

In the formulae and throughout the description, the term "alkynyl group" denotes a group which has one or more carbon-carbon triple bonds and has from 3 to 10 or from 3 to 6 or from 3 to 4 carbon atoms.

In the formulae and throughout the description, the term "alkylene" denotes a hydrocarbon group having from 1 to 10 or from 4 to 10 carbon atoms or from 5 to 10 carbon atoms and are connected to two silicon atoms. Exemplary alkylene groups include, but are not limited to, methylene (—CH$_2$—), ethylene (—CH$_2$CH$_2$—), propylene (—CH$_2$CH$_2$CH$_2$—), iso-propylene (—CH(Me)CH$_2$—).

In the formulae and throughout the description, the term "dialkylamino" denotes a nitrogen bonded to two hydrocarbon group having from 1 to 10 or from 4 to 10 carbon atoms or from 5 to 10 carbon atoms. Exemplary alkyl groups include, but are not limited to, dimethylamino, diethylamino, di-n-propylamino, di-iso-propylamino, di-sec-butylamino.

In the formulae and throughout the description, the term "cyclic alkylamino" denotes a nitrogen bonded to two carbon atoms in a cyclic ring having from 3 to 10 or from 4 to 10 carbon atoms or from 5 to 10 carbon atoms. Exemplary cyclicamino groups include, but are not limited to, piperidino, 2,6-dimethylpiperidino, pyrrolidino, 2,5-dimethylpyrrolidino.

In certain embodiments, one or more of the alkyl group, alkenyl group, alkynyl group, and/or aryl group in the Formulae IA, IB, and IC may be substituted or have one or more atoms or group of atoms substituted in place of, for example, a hydrogen atom. Exemplary substituents include, but are not limited to, oxygen, sulfur, halogen atoms (e.g., F, Cl, I, or Br), nitrogen, and phosphorous. In other embodiments, one or more of the alkyl group, alkenyl group, alkynyl group, alkoxy group, dialkylamino aryl group, and/or electron withdrawing group in Formula I may be unsubstituted.

Without being bound by theory, it is believed that aza-polysilane precursors such as those aza-polysilanes having Formulae IA, IB, and IC described herein comprising one or more of the following: a Si—N bond, a Si—Si bond, and at least two SiH$_2$ groups, or combinations thereof are advantageous over known aza-polysilane precursors containing only Si—N and Si—Si bonds or only Si—Cl and Si—Si bonds. In this regard, it is believed that the aza-polysilanes described herein having four or five SiH groups, one Si—N bond and one Si—Si bond make them more reactive than other aza-polysilane precursors, allowing deposition temperatures to be lower than other known aza-polysilanes, such as, for example, hexachlorodisilane. It is believed that the unique structures of the Formulae IA, IB, and IC precursors described herein allow for deposition temperatures of 400° C. or less, 300° C. or less, 200° C. or less, 100° C. or less, or 25° C.

In certain embodiments, the aza-polysilanes having Formulae IA, IB, and IC can be prepared by reacting a monochlorodisilane (MCDS) or monobromodisilane (MBDS) or lower molecular dialkylaminodisilane such as di-iso-propylaminodisilane or di-sec-butylaminodisilane with a primary amine having the following Formula II in an organic solvent or solvent mixture.

$$R^1\text{—NH}_2 \; R^2\text{—NH}_2 \qquad \text{II}$$

In Formula II, $R^1$ and $R^2$ are the same as in the substituents described in Formulae IA and IB. The following Equation 1 provide a non-limiting example of a reaction schemes or synthesis route which may be used to make the aza-polysilanes having Formulae IA and IB described herein. The reaction in Equation (1) can be conducted with (e.g., in the presence of) or without (e.g., in the absence of) organic solvents. In embodiments wherein an organic solvent is used, examples of suitable organic solvents include, but are not limited to, hydrocarbon such as hexanes, octane, toluene, and ethers such as diethylether and tetrahydrofuran (THF). In these or other embodiments, the reaction temperature is in the range of from about −70° C. to the boiling point of the solvent employed if a solvent is used. The resulting aza-polysilane can be purified, for example, via vacuum distillation after removing all by-products as well as any solvent(s) if present.

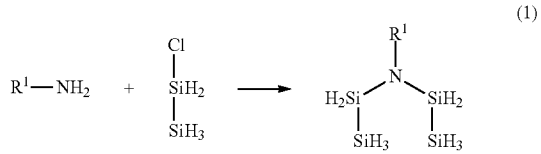

(1)

Equation 1 is one synthetic route to make the aza-polysilanes having Formula IA involving a reaction between monohalidodisilane (XSiH$_2$SiH$_3$ wherein X=Cl, Br, I) and a secondary amine presented in Formula II. Other synthetic routes may be also employed to make these aza-polysilanes as disclosed in the prior art, the reference entitled "Disilanyl-amines—Compounds Comprising the Structure Unit Si—Si—N, as Single-Source Precursors for Plasma-Enhanced Chemical Vapor Deposition (PE-CVD) of Silicon Nitride", Schuh et al., Zeitschrift Für Anorganische and Allgemeine Chemie, 619 (1993), pp. 1347-52.

The method used to form the silicon-containing films or coatings are deposition processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via atomic layer deposition (ALD), plasma enhanced ALD (PEALD) or plasma enhanced cyclic CVD (PECCVD) process. As used herein, the term "chemical vapor deposition processes" refers to any process wherein a substrate is exposed to one or more volatile precursors, which react and/or decompose on the substrate surface to produce the desired deposition. As used herein, the term "atomic layer deposition process" refers to a self-limiting (e.g., the amount of film material deposited in each reaction cycle is constant), sequential surface chemistry that deposits films of materials onto substrates of varying compositions. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator. In one embodiment, the silicon-containing film is deposited using an ALD process. In another embodiment, the silicon-containing film is deposited using a CCVD process. In a further embodiment, the silicon-containing film is deposited using a thermal CVD process. The term "reactor" as used herein, includes without limitation, reaction chamber or deposition chamber.

In certain embodiments, the method disclosed herein avoids pre-reaction of the precursors by using ALD or CCVD methods that separate the precursors prior to and/or during the introduction to the reactor. In this connection, deposition techniques such as ALD or CCVD processes are used to deposit the silicon-containing film. In one embodiment, the film is deposited via an ALD process by exposing the substrate surface alternatively to the one or more the silicon-containing precursor, oxygen-containing source, nitrogen-containing source, or other precursor or reagent. Film growth proceeds by self-limiting control of surface reaction, the pulse length of each precursor or reagent, and the deposition temperature. However, once the surface of the substrate is saturated, the film growth ceases.

In certain embodiments, the method described herein further comprises one or more additional silicon-containing precursors other than the aza-polysilane precursor having the above Formulae IA, IB, and IC. Examples of additional silicon-containing precursors include, but are not limited to, silane, disilane, monoaminosilane (e.g., di-iso-propylaminosilane, di-sec-butylaminosilane, phenylmethylaminosilane; organo-silicon compounds such as trisilylamine (TSA); monoaminosilane (di-iso-propylaminosilane, di-sec-butylaminosilane, phenylmethylaminosilane); siloxanes (e.g., hexamethyl disiloxane (HMDSO) and dimethyl siloxane (DMSO)); organosilanes (e.g., methylsilane, dimethylsilane, diethylsilane, vinyl trimethylsilane, trimethylsilane, tetramethylsilane, ethylsilane, disilylmethane, 2,4-disilapentane, 1,4-disilabutane, 2,5-disilahexane, 2,2-disilylpropane, 1,3,5-trisilacyclohexane and fluorinated derivatives of these compounds); phenyl-containing organo-silicon compounds (e.g., dimethylphenylsilane and diphenylmethylsilane); oxygen-containing organo-silicon compounds, e.g., dim ethyldimethoxysilane; 1,3,5,7-tetramethylcyclotetrasiloxane; 1,1,3,3-tetramethyldisiloxane; 1,3,5,7-tetrasila-4-oxo-heptane; 2,4,6,8-tetrasila-3,7-dioxo-nonane; 2,2-dimethyl-2,4,6,8-tetrasila-3,7-dioxo-nonane; octamethylcyclotetrasiloxane; [1,3,5,7,9]-pentamethylcyclopentasiloxane; 1,3,5,7-tetrasila-2,6-dioxo-cyclooctane; hexamethylcyclotrisiloxane; 1,3-dimethyldisiloxane; 1,3,5,7,9-pentamethylcyclopentasiloxane; hexamethoxydisiloxane, and fluorinated derivatives of these compounds.

Depending upon the deposition method, in certain embodiments, the one or more silicon-containing precursors may be introduced into the reactor at a predetermined molar volume, or from about 0.1 to about 1000 micromoles. In this or other embodiments, the silicon-containing and/or aza-polysilane precursor may be introduced into the reactor for a predetermined time period. In certain embodiments, the time period ranges from about 0.001 to about 500 seconds.

In certain embodiments, the silicon-containing films deposited using the methods described herein are formed in the presence of oxygen using an oxygen-containing source, reagent or precursor comprising oxygen. An oxygen-containing source may be introduced into the reactor in the form of at least one oxygen-containing source and/or may be present incidentally in the other precursors used in the deposition process. Suitable oxygen-containing source gases may include, for example, water (H$_2$O) (e.g., deionized water, purifier water, and/or distilled water), oxygen (O$_2$), oxygen plasma, water plasma, ozone (O$_3$), NO, N$_2$O, NO$_2$, carbon monoxide (CO), carbon dioxide (CO$_2$), CO$_2$ plasma, and combinations thereof. In certain embodiments, the oxygen-containing source comprises an oxygen-containing source gas that is introduced into the reactor at a flow rate ranging from about 1 to about 2000 square cubic centimeters (sccm) or from about 1 to about 1000 sccm. The oxygen-containing source can be introduced for a time that ranges from about 0.1 to about 100 seconds. In one particular embodiment, the oxygen-containing source comprises water having a temperature of 10° C. or greater. In embodiments wherein the film is deposited by an ALD or a cyclic CVD process, the precursor pulse can have a pulse duration that is greater than 0.01 seconds, and the oxygen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between. The oxygen-containing source or reagent is provided in a molecular amount less than a 1:1 ratio to the silicon precursor, so that at least some carbon is retained in the as deposited silicon-containing film.

In certain embodiments, the silicon-containing films comprise silicon and nitrogen. In these embodiments, the silicon-containing films deposited using the methods described herein are formed in the presence of nitrogen-containing source. A nitrogen-containing source may be introduced into the reactor in the form of at least one nitrogen-containing source and/or may be present incidentally in the other precursors used in the deposition process. Suitable nitrogen-containing source gases may include, for example, ammonia, hydrazine, monoalkylhydrazine, dialkylhydrazine, nitrogen, nitrogen/hydrogen, ammonia plasma, nitrogen plasma, nitrogen/argon plasma, nitrogen/helium plasma, nitrogen/hydrogen plasma, and mixture thereof. In certain embodiments, the nitrogen-containing source comprises an ammonia plasma or hydrogen/nitrogen plasma source gas that is introduced into the reactor at a flow rate ranging from about 1 to about 2000 square cubic centimeters (sccm) or from about 1 to about 1000 sccm. The nitrogen-containing source can be introduced for a time that ranges from about 0.1 to about 100 seconds. In embodiments wherein the film is deposited by an ALD or a cyclic CVD process, the precursor pulse can have a pulse duration that is greater than 0.01 seconds, and the nitrogen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between.

The deposition methods disclosed herein may involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon, hydrogen ($H_2$), and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

The respective step of supplying the precursors, oxygen-containing source, the nitrogen-containing source, and/or other precursors, source gases, and/or reagents may be performed by changing the time for supplying them to change the stoichiometric composition of the resulting silicon-containing film.

Energy is applied to the at least one of the precursor, nitrogen-containing source, reducing agent, other precursors or combination thereof to induce reaction and to form the silicon-containing film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The aza-polysilane precursors and/or other silicon-containing precursors may be delivered to the reaction chamber such as a CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

For those embodiments wherein the precursor(s) described herein is used in a composition comprising a solvent and an aza-polysilane precursor having Formulae IA, IB, and IC described herein, the solvent or mixture thereof selected does not react with the aza-polysilane. The amount of solvent by weight percentage in the composition ranges from 0.5% by weight to 99.5% or from 10% by weight to 75%. In this or other embodiments, the solvent has a boiling point (b.p.) similar to the b.p. of the aza-polysilane of Formulae IA, IB, or IC or the difference between the b.p. of the solvent and the b.p. of the azapolysilane is 40° C. or less, 30° C. or less, or 20° C. or less, or 10° C. Alternatively, the difference between the boiling points ranges from any one or more of the following end-points: 0, 10, 20, 30, or 40° C. Examples of suitable ranges of b.p. difference include without limitation, 0 to 40° C., 20° to 30° C., or 10° to 30° C. Examples of suitable solvents in the compositions include, but are not limited to, an ether (such as 1,4-dioxane, dibutyl ether), a tertiary amine (such as pyridine, 1-methylpiperidine, 1-ethylpiperidine, N,N'-Dimethylpiperazine, N,N,N',N'-Tetramethylethylenediamine), a nitrile (such as benzonitrile), an alkyl hydrocarbon (such as octane, nonane, dodecane, ethylcyclohexane), an aromatic hydrocarbon (such as toluene, mesitylene), a tertiary aminoether (such as bis(2-dimethylaminoethyl) ether), or mixtures thereof. Some non-limiting exemplary compositions include, but are not limited to, a composition comprising di-iso-3-tert-butyl-3-aza-pentasilane (b.p. about 150° C.) and octane (b.p. 125 to 126° C.), a mixture of di-iso-3-tert-butyl-3-aza-pentasilane (b.p. about 150° C.) and ethylcyclohexane (b.p. 130-132° C.), 1,4-bis(tert-butyl)-1,4-diaza-2,3,5,6-tetrasilacyclohexane (b.p. about 200° C. and 2,2'-oxybis(N,N-dimethylethanamine (b.p., 189° C.). In some embodiment, the solvent may stabilize the aza-polysilane of Formula IA, IB, and IC, then extending shelf-life of the aza-polysilane.

In another embodiment, a vessel for depositing a silicon-containing film comprising one or more aza-polysilane precursor having Formulae IA, IB, and IC is described herein. In one particular embodiment, the vessel comprises at least one pressurizable vessel (preferably of stainless steel) fitted with the proper valves and fittings to allow the delivery of one or more precursors to the reactor for a CVD or an ALD process. In this or other embodiments, the aza-polysilane precursor having Formulae IA, IB, and IC is provided in a pressurizable vessel comprised of stainless steel and the purity of the precursor is 98% by weight or greater or 99.5% or greater which is suitable for the majority of semiconductor applications. In certain embodiments, such vessels can also have means for mixing the precursors with one or more additional precursor if desired. In these or other embodiments, the contents of the vessel(s) can be premixed with an additional precursor. Alternatively, the aza-polysilane precursor and/or other precursor can be maintained in separate vessels or in a single vessel having separation means for maintaining the aza-polysilane precursor and other precursor separate during storage.

In one embodiment of the method described herein, a cyclic deposition process such as CCVD, ALD, or PEALD may be employed, wherein at least one silicon-containing precursor selected from an aza-polysilane precursor having the formula described herein and optionally a nitrogen-containing source such as, for example, ammonia, hydrazine, monoalkylhydrazine, dialkylhydrazine, nitrogen, nitrogen/hydrogen, ammonia plasma, nitrogen plasma, nitrogen/hydrogen plasma are employed.

In certain embodiments, the gas lines connecting from the precursor canisters to the reaction chamber are heated to one or more temperatures depending upon the process requirements and the container of the aza-polysilane precursor having the formula I described herein is kept at one or more temperatures for bubbling. In other embodiments, a solution comprising the at least one silicon-containing precursor having the formula described herein is injected into a vaporizer kept at one or more temperatures for direct liquid injection.

A flow of argon and/or other gas may be employed as a carrier gas to help deliver the vapor of the at least one aza-polysilane precursor to the reaction chamber during the precursor pulsing. In certain embodiments, the reaction chamber process pressure is about 1 Torr.

In a typical ALD or CCVD process, a substrate such as, without limitation, a silicon oxide, carbon doped silicon oxide, flexible substrate, or metal nitride substrate is heated on a heater stage in a reaction chamber that is exposed to the silicon-containing precursor initially to allow the aza-polysilane to chemically adsorb onto the surface of the substrate. A purge gas such as nitrogen, argon, or other inert gas purges away unabsorbed excess aza-polysilane from the process chamber. After sufficient purging, an oxygen-containing source may be introduced into reaction chamber to react with the absorbed surface followed by another gas purge to remove reaction by-products from the chamber. The process cycle can be repeated to achieve the desired film thickness. In other embodiments, pumping under vacuum can be used to remove unabsorbed excess aza-polysilane from the process chamber, after sufficient evacuation under pumping, an oxygen-containing source may be introduced into reaction chamber to react with the absorbed surface followed by another pumping down purge to remove reaction by-products from the chamber. In yet another embodiment, the aza-polysilane and the oxygen-containing source can be co-flowed into reaction chamber to react on the substrate surface to deposit silicon oxide, carbon doped silicon oxide. In a certain embodiment of cyclic CVD, the purge step is not used.

In this or other embodiments, it is understood that the steps of the methods described herein may be performed in a variety of orders, may be performed sequentially or concurrently (e.g., during at least a portion of another step), and any combination thereof. The respective step of supplying the precursors and the nitrogen-containing source gases may be performed by varying the duration of the time for supplying them to change the stoichiometric composition of the resulting silicon-containing film.

In another embodiment of the method disclosed herein, the films containing both silicon and nitrogen are formed using an ALD, PEALD, CCVD or PECCVD deposition method that comprises the steps of:

a. providing a substrate in an ALD reactor;

b. introducing into the ALD reactor at least one aza-polysilane precursor comprising at least two Si—N bonds, at least one Si—Si bond, and at least two $SiH_2$ groups represented by the following Formulae IA, IB, IC:

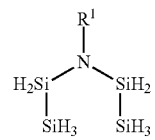

IA

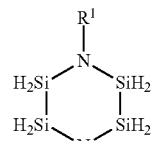

IB

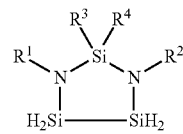

IC wherein $R^1$ and $R^2$ are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group;

c. chemisorbing the at least one aza-polysilane precursor onto a substrate;

d. purging away the unreacted at least one aza-polysilane precursor using a purge gas;

e. providing a nitrogen-containing source to the aza-polysilane precursor onto the heated substrate to react with the sorbed at least one aza-polysilane precursor; and f. optionally purging or pumping away any unreacted nitrogen-containing source.

In another aspect, there is provided a method of forming a film selected from a silicon oxide and a carbon doped silicon oxide film via a PEALD or a PECCVD deposition process, the method comprising the steps of:

a. providing a substrate in a reactor;

b. introducing into the reactor oxygen along with at least one aza-polysilane precursor comprising at least two Si—N bonds, at least one Si—Si bond, and at least two SiH$_2$ groups represented by the following Formulae IA, IB, IC:

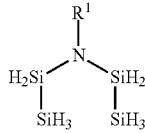

IA

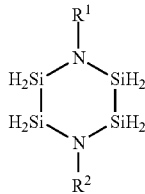

IB

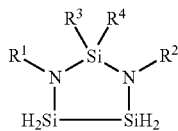

IC wherein R$^1$ and R$^2$ are independently selected from a linear or branched C$_1$ to C$_{10}$ alkyl group, a linear or branched C$_3$ to C$_{10}$ alkenyl group, a linear or branched C$_3$ to C$_{10}$ alkynyl group, C$_3$ to C$_{10}$ cyclic alkyl group, C$_3$ to C$_{10}$ hetero-cyclic alkyl group, a C$_5$ to C$_{10}$ aryl group, a C$_3$ to C$_{10}$ hetero-aryl group, a C$_2$ to C$_{10}$ dialkylamino group, and a C$_3$ to C$_{10}$ cyclic alkylamino group; R$^3$ and R$^4$ are independently selected from hydrogen, a linear or branched C$_1$ to C$_{10}$ alkyl group, a linear or branched C$_2$ to C$_{10}$ alkenyl group, a linear or branched C$_2$ to C$_{10}$ alkynyl group, C$_3$ to C$_{10}$ cyclic alkyl group, C$_3$ to C$_{10}$ hetero-cyclic alkyl group, a C$_5$ to C$_{10}$ aryl group, and a C$_3$ to C$_{10}$ hetero-aryl group, a C$_2$ to C$_{10}$ dialkylamino group, and a C$_3$ to C$_{10}$ cyclic alkylamino group;

c. purging the reactor with a purge gas along with oxygen;

d. applying RF plasma;

e. purging the reactor with a purge gas or pumping the reactor to remove unreacted aza-polysilane and any reaction by-products; and wherein steps b through e are repeated until a desired thickness of the film is obtained.

In another embodiment of the method disclosed herein, the silicon-containing films is formed using a ALD deposition method that comprises the steps of:

a. providing a substrate in a reactor;

b. introducing into the reactor at least one aza-polysilane precursor comprising at least two Si—N bonds, at least one Si—Si bond, and at least two SiH$_2$ groups represented by the following Formulae IA, IB, IC:

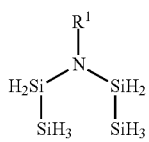

IA

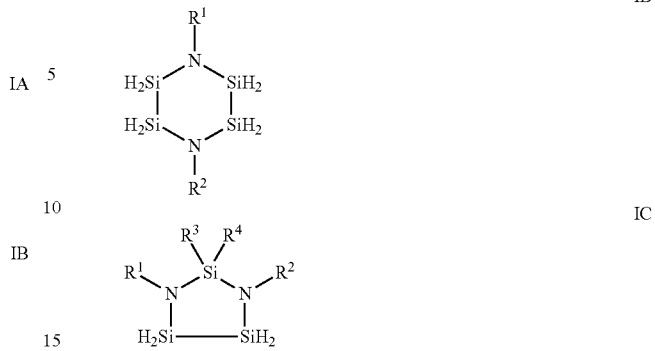

IB

IC wherein R$^1$ and R$^2$ are independently selected from a linear or branched C$_1$ to C$_{10}$ alkyl group, a linear or branched C$_3$ to C$_{10}$ alkenyl group, a linear or branched C$_3$ to C$_{10}$ alkynyl group, C$_3$ to C$_{10}$ cyclic alkyl group, C$_3$ to C$_{10}$ hetero-cyclic alkyl group, a C$_5$ to C$_{10}$ aryl group, a C$_3$ to C$_{10}$ hetero-aryl group, a C$_2$ to C$_{10}$ dialkylamino group, and a C$_3$ to C$_{10}$ cyclic alkylamino group; R$^3$ and R$^4$ are independently selected from hydrogen, a linear or branched C$_1$ to C$_{10}$ alkyl group, a linear or branched C$_2$ to C$_{10}$ alkenyl group, a linear or branched C$_2$ to C$_{10}$ alkynyl group, C$_3$ to C$_{10}$ cyclic alkyl group, C$_3$ to C$_{10}$ hetero-cyclic alkyl group, a C$_5$ to C$_{10}$ aryl group, and a C$_3$ to C$_{10}$ hetero-aryl group, a C$_2$ to C$_{10}$ dialkylamino group, and a C$_3$ to C$_{10}$ cyclic alkylamino group;

c. chemisorbing the at least one aza-polysilane precursor onto a substrate;

d. purging away the unreacted at least one aza-polysilane precursor using a purge gas;

e. providing an oxygen-containing source to the aza-polysilane precursor onto the heated substrate to react with the sorbed at least one aza-polysilane precursor; and f. optionally purging or pumping away any unreacted oxygen-containing source.

In another aspect, there is provided a method of forming a silicon nitride or silicon carbonitride film via PEALD or PECCVD process, the method comprising the steps of:

a. providing a substrate in a reactor;

b. introducing into the reactor a nitrogen-containing source and at least one aza-polysilane precursor comprising at least two Si—N bonds, at least one Si—Si bond, and at least two SiH$_2$ groups represented by the following Formulae IA, IB, IC:

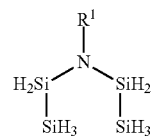

IA

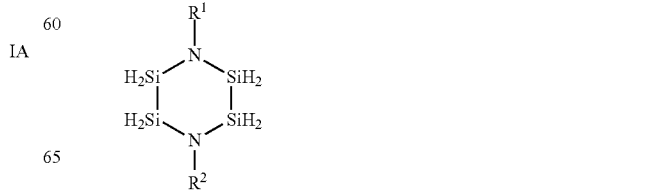

IB

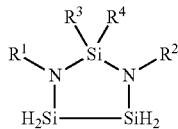

IC wherein R¹ and R² are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; R³ and R⁴ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group;

c. purging the reactor with a purge gas along with the nitrogen-containing source;

d. applying RF plasma; and e. purging the reactor with a purge gas or pumping the reactor to remove unreacted aza-polysilane and any by-products; and wherein steps b through e are repeated until a desired thickness of the film is obtained.

The above steps define one cycle for the method described herein; and the cycle can be repeated until the desired thickness of a silicon-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen-containing source may be performed by varying the duration of the time for supplying them to change the stoichiometric composition of the resulting silicon-containing film, although always using oxygen in less than a stoichiometric amount relative to the available silicon.

For multi-component silicon-containing films, other precursors such as silicon-containing precursors, nitrogen-containing precursors, reducing agents, or other reagents can be alternately introduced into the reactor chamber.

In a further embodiment of the method described herein, the silicon-containing film is deposited using a thermal CVD process. In this embodiment, the method comprises:

a. placing one or more substrates into a reactor which is heated to one or more temperatures ranging from ambient temperature to about 700° C.;

b. introducing at least one aza-polysilane precursor comprising at least two Si—N bonds, at least one Si—Si bond, and at least two SiH₂ groups represented by the following Formulae IA, IB, IC:

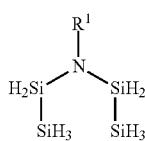

IA

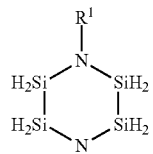

IB

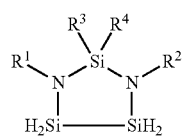

IC wherein R¹ and R² are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; R³ and R⁴ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group; and c. providing an oxygen-containing source into the reactor to at least partially react with the at least one aza-polysilane precursor and deposit a silicon-containing film onto the one or more substrates. In certain embodiments of the CVD method, the reactor is maintained at a pressure ranging from 10 mTorr to 760 Torr during the introducing step. The above steps define one cycle for the method described herein; and the cycle can be repeated until the desired thickness of a silicon-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen-containing source may be performed by varying the duration of the time for supplying them to change the stoichiometric composition of the resulting silicon-containing film, although always using oxygen in less than a stoichiometric amount relative to the available silicon.

In a further embodiment of the method described herein, an amorphous or crystalline silicon film is deposited using the Formula I precursor described herein. In this embodiment, the method comprises:

a. placing one or more substrates into a reactor which is heated to a one or more temperatures ranging from ambient temperature to about 700° C.;

b. introducing at least one aza-polysilane precursor comprising at least two Si—N bonds, at least one Si—Si bond, and at least two SiH₂ groups represented by the following Formulae IA, IB, IC:

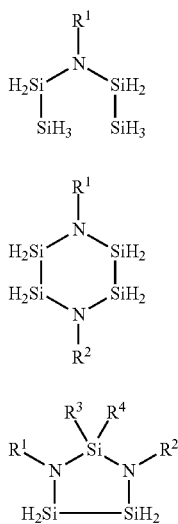

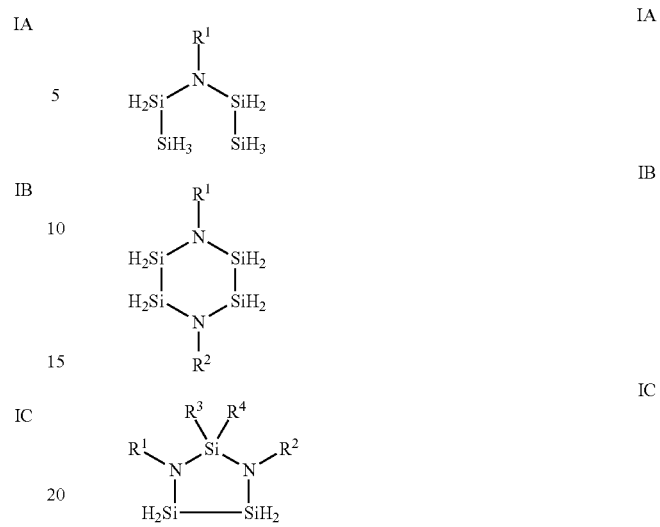

wherein $R^1$ and $R^2$ are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group; and c. providing a reducing agent source into the reactor to at least partially react with the at least one aza-polysilane precursor and deposit a silicon-containing film onto the one or more substrates. The reducing agent is selected from the group consisting of hydrogen, hydrogen plasma, helium plasma, argon plasma, hydrogen chloride. In certain embodiments of the CVD method, the reactor is maintained at a pressure ranging from 10 mTorr to 760 Torr during the introducing step. The above steps define one cycle for the method described herein; and the cycle can be repeated until the desired thickness of a film is obtained.

For multi-component silicon-containing films, other precursors such as silicon-containing precursors, nitrogen-containing precursors, oxygen-containing sources, reducing agents, and/or other reagents can be alternately introduced into the reactor chamber.

In a further embodiment of the method described herein, the silicon-containing film is deposited using a thermal CVD process. In this embodiment, the method comprises:

a. placing one or more substrates into a reactor which is heated to one or more temperatures ranging from ambient temperature to about 700° C.;

b. introducing at least one aza-polysilane precursor comprising at least two Si—N bonds, at least one Si—Si bond, and at least two $SiH_2$ groups represented by the following Formula IA, IB, IC:

wherein $R^1$ and $R^2$ are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group; and c. providing a nitrogen-containing source into the reactor to at least partially react with the at least one aza-polysilane precursor and deposit a silicon-containing film onto the one or more substrates. In certain embodiments of the CVD method, the reactor is maintained at a pressure ranging from 10 mTorr to 760 Torr during the introducing step.

In a further embodiment of the method described herein, the aza-polysilane precursors are used for depositing a silicon containing film which is an amorphous film, a crystalline silicon film, or a mixture thereof. In these embodiments, the silicon containing films is formed using a deposition method selected from ALD or cyclic CVD that comprises the steps of:

placing a substrates into a reactor which is heated to a temperature ranging from ambient temperature to about 700° C. and maintained at a pressure of 1 Torr or less;

introducing at least one aza-polysilane precursor comprising at least two Si—N bonds, at least one Si—Si bond, and at least two $SiH_2$ groups represented by the following Formulae IA, IB, IC:

-continued

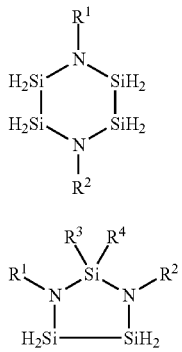

wherein $R^1$ and $R^2$ are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group; and providing a reducing agent into the reactor to at least partially react with the at least one organoaminosilane precursor and deposit a silicon containing film onto the one or more substrates wherein the reducing agent is at least one selected from the group consisting of hydrogen, hydrogen plasma, helium plasma, argon plasma, or hydrogen chloride. The above steps define one cycle for the method described herein; and the cycle can be repeated until the desired thickness of a silicon containing film is obtained. The desired thickness of the film can range from 1 Å to 10,000 Å.

In another aspect, there is provided a method of depositing amorphous or crystalline silicon film via an atomic layer deposition or cyclic chemical vapor deposition process or chemical vapor deposition at temperature lower than conventional silicon precursors, the method comprising the steps of:

a. providing a substrate in a reactor;

b. introducing into the reactor at least one aza-polysilane precursor comprising at least two Si—N bonds, at least one Si—Si bond, and at least two $SiH_2$ groups represented by the following Formula IA, IB, IC:

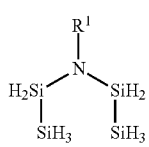

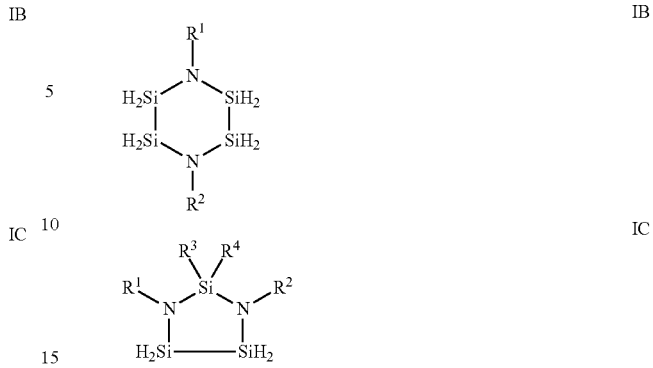

wherein $R^1$ and $R^2$ are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group;

c. purging the reactor with a purge gas wherein steps b through c are repeated until a desired thickness of the silicon film is obtained.

It is believed that the aza-polysilane precursors described herein can generate $H_2Si$: di-radicals or $H_3Si$ radical upon heating which can promote formation oligomers containing Si—Si bonds or anchor on the surface of a substrate. Those oligomers or anchored $SiH_2$ or $SiH_3$ can further form amorphous silicon films. In this or other embodiments, those oligomers function as a seed layer for subsequent deposition of silicon or silicon oxide films.

In certain embodiments, the aza-polysilane precursors described herein can also be used as a dopant for metal containing films, such as but not limited to, metal oxide films or metal nitride films. In these embodiments, the metal containing film is deposited using an ALD or CVD process such as those processes described herein using metal alkoxide, metal amide, or volatile organometallic precursors. Examples of suitable metal alkoxide precursors that may be used with the method disclosed herein include, but are not limited to, group 3 to 6 metal alkoxide, group 3 to 6 metal complexes having both alkoxy and alkyl substituted cyclopentadienyl ligands, group 3 to 6 metal complexes having both alkoxy and alkyl substituted pyrrolyl ligands, group 3 to 6 metal complexes having both alkoxy and diketonate ligands; group 3 to 6 metal complexes having both alkoxy and ketoester ligands; Examples of suitable metal amide precursors that may be used with the method disclosed herein include, but are not limited to, tetrakis(dimethylamino)zirconium (TDMAZ), tetrakis(diethylamino)zirconium (TDEAZ), tetrakis(ethylmethylamino)zirconium (TEMAZ), tetrakis(dimethylamino)hafnium (TDMAH), tetrakis(diethylamino)hafnium (TDEAH), and tetrakis(ethylmethylamino)hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino)tantalum (TBTDET), tert-butylimino tri(dimethylamino)tantalum (TBTDMT), tert-butylimino tri(ethylmethylamino)tantalum (TBTEMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino)tantalum, bis(tert-butylimino)bis(dimethylamino)tungsten (BTBMW), bis(tert-butylimino)bis(diethylamino)tungsten, bis(tert-butylimino)bis(ethylmethylamino)tungsten, and combinations thereof. Examples of suitable organometallic precursors that may be used with the method disclosed herein include, but are not limited to, group 3 metal cyclopentadienyls or alkyl cyclopentadienyls. Exemplary Group 3 to 6 metal herein include, but not limited to, Y, La, Ce, Pr, Nd, Sm, Eu, Gd, Tb, Dy, Er, Yb, Lu, Ti, Hf, Zr, V, Nb, Ta, Cr, Mo, and W.

In certain embodiments, the resultant silicon-containing films or coatings can be exposed to a post-deposition treatment such as, but not limited to, a plasma treatment, chemical treatment, ultraviolet light exposure, electron beam exposure, and/or other treatments to affect one or more properties of the film.

In certain embodiments, the silicon-containing films described herein have a dielectric constant of 6 or less. In these or other embodiments, the films can a dielectric constant of about 5 or below, or about 4 or below, or about 3.5 or below. However, it is envisioned that films having other dielectric constants (e.g., higher or lower) can be formed depending upon the desired end-use of the film. An example of the silicon containing or silicon-containing film that is formed using the aza-polysilane precursors and processes described herein has the formulation $Si_xO_yC_zN_v H_w$ wherein Si ranges from about 10% to about 40%; O ranges from about 0% to about 65%; C ranges from about 0% to about 75% or from about 0% to about 50%; N ranges from about 0% to about 75% or from about 0% to 50%; and H ranges from about 0% to about 50% atomic percent weight % wherein x+y+z+v+w=100 atomic weight percent, as determined for example, by XPS or other means.

As mentioned previously, the method described herein may be used to deposit a silicon-containing film on at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, a flexible substrate, organic polymers, porous organic and inorganic materials, metals such as copper and aluminum, and diffusion barrier layers such as but not limited to TiN, Ti(C)N, TaN, Ta(C)N, Ta, W, or WN. The films are compatible with a variety of subsequent processing steps such as, for example, chemical mechanical planarization (CMP) and anisotropic etching processes.

The deposited films have applications, which include, but are not limited to, computer chips, optical devices, magnetic information storages, coatings on a supporting material or substrate, microelectromechanical systems (MEMS), nanoelectromechanical systems, thin film transistor (TFT), light emitting diodes (LED), organic light emitting diodes (OLED), IGZO, and liquid crystal displays (LCD).

The following examples illustrate the method for preparing aza-polysilane precursors as well as depositing silicon-containing films described herein and are not intended to limit it in any way.

EXAMPLES

Example 1: Synthesis of 3-tert-butyl-3-aza-pentasilane

In a Schlenk flask equipped with magnetic stirring bar, 3 equivalent diisopropylaminodisilane (DIPADS) was mixed with 1 equivalent tert-butylamine. The reaction mixture was stirred at room temperature for 96 hours. The reaction was monitored with gas chromatography. When most of tert-butylamine was convered to N-silyl-tert-butylamine, the Schlenk flask was connected to a vacuum line. Byproduct diisopropylamine was removed by vacuum in order to drive the reaction to completion. The product 3-tert-butyl-3-aza-pentasilane was separated by fractional vacuum distillation.

Example 2: Synthesis of 3-tert-butyl-3-aza-pentasilane

In a 1 liter 3-necked round bottom flask equipped with an addition funnel, a condenser, and a mechanical stirrer, a solution of 60.6 g (0.6 mol) triethylamine and 21.9 g (0.3 mol) t-butylamine in 600 ml hexane was cooled to −20 C with a dry ice bath. With stirring, a solution of 57.9 g (0.6 mol) chlorodisilane in 100 ml hexane was added dropwise. Then the reaction mixture was allowed to warm to room temperature and stirred overnight. The solid byproduct triethylamine hydrochloride was removed by filtration. The solvent hexane was removed by distillation. The product 3-tert-butyl-3-aza-pentasilane was purified by vacuum distillation.

Example 3: Synthesis of 1,4-bis(tert-butyl)-1,4-diaza-2,3,5,6-tetrasilacyclohexane In a 2 liter 3-necked round bottom flask equipped with an addition funnel, a condenser, and a mechanical stirrer, a solution of 60.6 g (0.6 mol) triethylamine and 21.9 g (0.3 mol) t-butylamine in 1000 ml hexane was cooled to −20 C with a dry ice bath. With stirring, a solution of 39.3 g (0.3 mol) 1,2-dichlorodisilane in 200 ml hexane was added dropwise. Then the reaction mixture was allowed to warm to room temperature and stirred overnight. The solid byproduct triethylamine hydrochloride was removed by filtration. The solvent hexane was removed by distillation. The product 1,4-bis(tert-butyl)-1,4-diaza-2,3,5,6-tetrasilacyclohexane was purified by vacuum distillation as a colorless liquid, b.p. 55 C/0.05 torr.

Additional aza-polysilane precursors of Formula IA and IB were made via similar fashion between di-iso-propylaminodisilane with corresponding primary amines with Formula II described herein and were characterized by mass spectroscopy (MS). The molecular weight (MW), the structure, and corresponding MS fragmentation peaks of each organoaminosilane precursor are provided in Table 1 to confirm their identification.

TABLE 1

| Aza-polysilanes Having Formula IA and IB | | | |
|---|---|---|---|
| No. | Precursor Name | MW | Structure | MS Peaks |
| 1 | 3-iso-propyl-3-aza-pentasilane | 179.52 | 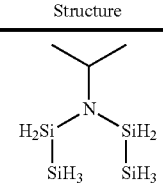 | 179, 164, 148, 136, 132, 116, 102, 86, 72 |

TABLE 1-continued

Aza-polysilanes Having Formula IA and IB

| No. | Precursor Name | MW | Structure | MS Peaks |
|---|---|---|---|---|
| 2 | 3-tert-butyl-3-aza-pentasilane | 193.54 | 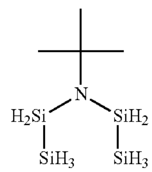 | 193, 178, 160, 146, 129, 116, 106, 98, 80, 70, 57 |
| 3 | 3-(piperidinyl-1-yl)-3-aza-pentasilane | 220.57 | 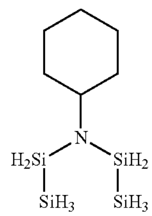 | 220, 189, 157, 146, 133, 114, 106, 98, 84, 72, 56 |
| 4 | 1,4-bis(tert-butyl)-1,4-diaza-2,3,5,6-tetrasilacyclohexane | 262.65 | 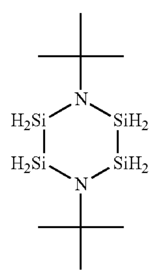 | 262, 247, 217, 203, 187, 173, 159, 144, 130, 114, 100, 86, 72, 58 |
| 5 | 3-(pyridin-2-yl)-3-aza-pentasilane | 214.52 | 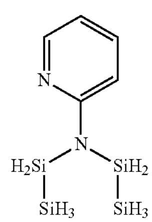 | 214, 183, 153, 121, 106, 94, 85, 78, 70, 58, 51, 44 |
| 6 | 3-(pyrimidin-2-yl)-3-aza-pentasilane | 215.51 | 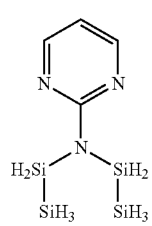 | 215, 184, 152, 122, 112, 99, 92, 82, 70, 58, |

Prophetic Example 4: Depositions of Si Containing Films Using 1,4-bis(tert-butyl)-1,4-diaza-2,3,5,6-tetrasilacyclohexane In the following prophetic examples, unless stated otherwise, properties are obtained from sample films deposited onto medium resistivity (14-17 Ω-cm) single crystal silicon wafer substrates. All film depositions are performed using 300 mm production tool, ASM Stellar 3000 with an ALD process listed in Table 2.

TABLE 2

Steps used in ALD depositions

| | Steps |
|---|---|
| a | providing a substrate in a reactor; |
| b | Introduce an aza-polysilane precursor to the reactor |
| c | Purge the aza-polysilane precursor with inert gas |
| d | Introducing plasma containing both nitrogen and noble gas |
| e | Purge $N_2$ plasma |

Refractive index and thickness for deposited film are measured using ellipsometer. Film structure and composition are analyzed using Fourier Transform Infrared (FTIR) spectroscopy and X-Ray Photoelectron Spectroscopy (XPS) while density is measured with X-ray Reflectometry (XRR).

Atomic layer deposition is performed using 1,4-bis(tert-butyl)-1,4-diaza-2,3,5,6-tetrasilacyclohexane as the aza-polysilane precursor and $Ar/N_2$ plasma. The silicon wafer is heated to 300° C. Deposition process is performed using steps described in Table 2, repeated 1000 times, using the following conditions:
  a) providing a substrate in a reactor;
  b) Introducing silicon containing precursor: 1,4-bis(tert-butyl)-1,4-diaza-2,3,5,6-tetrasilacyclohexane as the aza-polysilane precursor
    Chamber pressure: 2 Torr
    the aza-polysilane precursor pulse: 2 and 5 seconds
  c) Inert gas purge
    Argon flow: 300 sccm
    Chamber pressure: 2 Torr
    Purge time: 2 seconds
  d) Introducing plasma containing both nitrogen and noble gas
    Argon flow: 300 sccm
    Nitrogen flow: 400 sccm
    Chamber pressure: 2 Torr
    Plasma power: 500 W
    Plasma time: 5 seconds
  e) Purge plasma
    Argon flow: 300 sccm
    Chamber pressure: 2 Torr
    Purge time: 2 seconds The resulting Si containing films are characterized to contain silicon and nitrogen.

The invention claimed is:
1. A method for forming a silicon and nitrogen containing film on at least one surface of a substrate by an atomic layer deposition process, the method comprising:
  providing the at least one surface of the substrate in a reaction chamber;
  introducing at least one aza-polysilane precursor comprising at least two Si—N bonds, at least one Si—Si bond, and at least two $SiH_2$ groups represented by the following Formulae IA, IB, and IC:

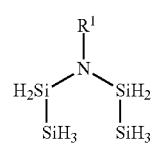

IA

-continued

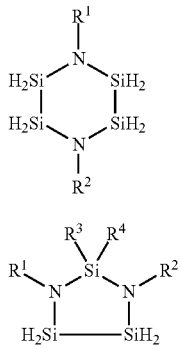

wherein $R^1$ and $R^2$ are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_6$ cyclic alkylamino group; $R^3$ and $R^4$ are independently selected from hydrogen, a linear or branched $C_1$ to $C_{10}$ alkyl group, a linear or branched $C_2$ to $C_{10}$ alkenyl group, a linear or branched $C_2$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, and a $C_3$ to $C_{10}$ hetero-aryl group, a $C_2$ to $C_{10}$ dialkylamino group, and a $C_3$ to $C_{10}$ cyclic alkylamino group wherein the aza-polysilane precursor is prepared by reacting at least one of a monochlorodisilane, monobromodisilane and dialkylaminodisilane with a primary amine; and introducing a nitrogen-containing source into the reactor wherein the at least one aza-polysilane precursor and the nitrogen-containing source react at a temperature of less than 300 C under atomic layer deposition process conditions to form the film on the at least one surface; and wherein when the at least one aza-polysilane precursor is represented by Formula 1B $R^1$ and $R^2$ in Formula IB cannot both be iso-propyl, tert-butyl, or benzyl.

2. The method of claim 1 wherein the precursor further comprises a solvent wherein the solvent has a boiling point and wherein the difference between the boiling point of the solvent and that of the at least one aza-polysilane is 40° C. or less.

3. The method of claim 2 wherein the solvent comprises at least one selected from the group consisting of ether, tertiary amine, alkyl hydrocarbon, aromatic hydrocarbon, tertiary aminoether.

4. The method of claim 1 wherein the at least one aza-polysilane precursor is selected from the group consisting of 3-iso-propyl-3-aza-pentasilane, 3-tert-butyl-3-aza-pentasilane, 3-tert-pentyl-3-aza-pentasilane, 3-cyclopentyl-3-aza-pentasilane, 3-cyclohexyl-3-aza-pentasilane, 3-(2,6-dimethylcyclohexyl-3-aza-pentasilane, 3-(tetrahydropyran-4-yl)-3-aza-pentasilane, 3-(1-methylpiperidin-4-yl)-3-aza-pentasilane, 3-phenyl-3-aza-pentasilane, 3-(2-methyl-tolyl)-3-aza-pentasilane, 3-(2,6-dimethyl-tolyl)-3-aza-pentasilane, 3-(pyridin-3-yl)-3-aza-pentasilane, 3-(4-methylpyridin-3-yl)-3-aza-pentasilane 1,4-bis(cyclopentyl)-1,4-diaza-2,3,5,6-tetrasilacyclohexane, 1,4-bis(cyclohexyl)-1,4-diaza-2,3,5,6-tetrasilacyclohexane, 1,4-bis(2,6-dimethylcyclohexyl)-1,4-Diaza-2,3,5,6-tetrasilacyclohexane, 1,4-bis(iso-propyl)-1,4-diaza-2,3,5,6-tetrasilacyclohexane, 1,4-bis(tert-butyl)-1,4-diaza-2,3,5,6-tetrasilacyclohexane, 1,4-bis(tert-pentyl)-1,4-diaza-2,3,5,6-tetrasilacyclohexane.

5. The method of claim 1 wherein the dialkylaminodisilane comprises di-iso-propylaminodisilane.

6. A method of forming a silicon-containing film via an atomic layer deposition (ALD) process, the method comprising the steps of:
a. providing a substrate in an ALD reactor wherein the substrate is heated to a temperature of less than about 300C;
b. providing in the ALD reactor at least one aza-polysilane precursor represented by the following Formula

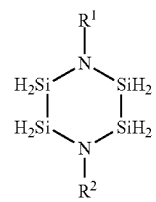

wherein $R^1$ and $R^2$ are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group;
c. purging the ALD reactor with an inert gas;
d. alternatively providing at least one of the aza-polysilane precursor, an oxygen-containing source and a nitrogen-containing source in the ALD reactor;
e. purging the ALD reactor with an inert gas; and wherein steps b through e are repeated under ALD process conditions until a desired thickness of the film is obtained wherein the at least one aza-polysilane precursor comprises at least one member selected from the group consisting of 1,4-bis(cyclopentyl)-1,4-diaza-2,3,5,6-tetrasilacyclohexane, 1,4-bis(cyclohexyl)-1,4-diaza-2,3,5,6-tetrasilacyclohexane, 1,4-bis(2,6-dimethylcyclohexyl)-1,4-Diaza-2,3,5,6-tetrasilacyclohexane, 1,4-bis(iso-propyl)-1,4-diaza-2,3,5,6-tetrasilacyclohexane, 1,4-bis(tert-butyl)-1,4-diaza-2,3,5,6-tetrasilacyclohexane, and 1,4-bis(tert-pentyl)-1,4-diaza-2,3,5,6-tetrasilacyclohexane and wherein the aza-polysilane precursor is prepared by reacting at least one of a monochlorodisilane, monobromodisilane or dialkylaminodisilane with a primary amine.

7. The method of claim 6 wherein the reacting step is conducted at a temperature of 200° C. or less.

8. The method of claim 6 wherein the reacting step is conducted at a temperature of 100° C. or less.

9. The method of claim 6 wherein the reacting step is conducted at 50° C. or less.

10. The method of claim 6 wherein the method further comprises at least one post-deposition treatment.

11. A method of forming a silicon-containing film onto at least a surface of a substrate using a plasma enhanced atomic layer (PEALD) deposition process, the method comprising:
a. providing a substrate in an ALD reactor;
b. providing in the ALD reactor at least one aza-polysilane precursor comprising at least two Si—N bonds, at least one Si—Si bond, and at least two $SiH_2$ groups represented by the following Formulae:

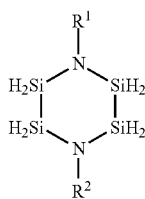

wherein R¹ and R² are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group wherein the aza-polysilane precursor is prepared by reacting at least one of a monochlorodisilane, monobromodisilane and dialkylaminodisilane with a primary amine;

c. purging the ALD reactor with an inert gas;
d. providing a plasma nitrogen-containing source in the ALD reactor;
e. purging the ALD reactor with an inert gas; and wherein the steps b through e are repeated using the PEALD deposition process until a desired thickness of the silicon-containing film is obtained.

12. The method of claim 11 wherein the at least one aza-polysilane precursor is selected from the group consisting of 1,4-bis(cyclopentyl)-1,4-diaza-2,3,5,6-tetrasilacyclohexane, 1,4-bis(cyclohexyl)-1,4-diaza-2,3,5,6-tetrasilacyclohexane, 1,4-bis(2,6-dimethylcyclohexyl)-1,4-Diaza-2,3,5,6-tetrasilacyclohexane, 1,4-bis(iso-propyl)-1,4-diaza-2,3,5,6-tetrasilacyclohexane, 1,4-bis(tert-butyl)-1,4-diaza-2,3,5,6-tetrasilacyclohexane, 1,4-bis(tert-pentyl)-1,4-diaza-2,3,5,6-tetrasilacyclohexane.

13. A method of forming a silicon-containing film via an atomic layer deposition (ALD) process, the method comprising the steps of:
a. providing a substrate in an ALD reactor;
b. providing in the ALD reactor at least one aza-polysilane precursor represented by the following Formula IB:

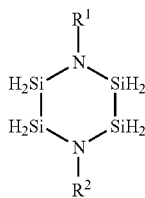

wherein R¹ and R² are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group and is prepared by reacting at least one of a monochlorodisilane, monobromodisilane or dialkylaminodisilane with a primary amine;
c. purging the ALD reactor with an inert gas;
d. alternatively providing the aza-polysilane precursor, an oxygen-containing source and a nitrogen-containing source in the ALD reactor;
e. purging the ALD reactor with an inert gas; and wherein steps b through e are repeated under ALD process conditions until a desired thickness of the film is obtained.

14. The method of claim 13 wherein the at least one aza-polysilane precursor is selected from the group consisting of 1,4-bis(cyclopentyl)-1,4-diaza-2,3,5,6-tetrasilacyclohexane, 1,4-bis(cyclohexyl)-1,4-diaza-2,3,5,6-tetrasilacyclohexane, 1,4-bis(2,6-dimethylcyclohexyl)-1,4-Diaza-2,3,5,6-tetrasilacyclohexane, 1,4-bis(iso-propyl)-1,4-diaza-2,3,5,6-tetrasilacyclohexane, 1,4-bis(tert-butyl)-1,4-diaza-2,3,5,6-tetrasilacyclohexane, and 1,4-bis(tert-pentyl)-1,4-diaza-2,3,5,6-tetrasilacyclohexane.

15. The method of claim 13 wherein the ALD process is a plasma enhanced atomic layer (PEALD) process.

16. The method of claim 13 wherein the method further comprises at least one post-deposition treatment.

17. The method of claim 13 wherein the silicon containing film comprises silicon oxide.

18. The method of claim 13 wherein the nitrogen-containing source is selected from the group consisting of ammonia, hydrazine, monoalkylhydrazine, dialkylhydrazine, nitrogen, nitrogen/hydrogen, ammonia plasma, nitrogen plasma, nitrogen/hydrogen plasma, nitrogen/helium plasma, nitrogen/argon plasma, helium plasma, argon plasma, hydrogen plasma, and mixtures thereof.

19. The method of claim 13 wherein the silicon-containing film is selected from the group consisting of silicon nitride and silicon carbonitride.

20. A method of forming a silicon-containing film via an atomic layer deposition (ALD) process, the method comprising the steps of:
a. providing a substrate in an ALD reactor wherein the substrate is heated to a temperature of less than about 300 C;
b. providing in the ALD reactor at least one aza-polysilane precursor represented by the following Formula

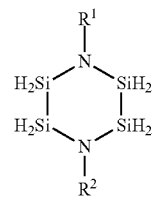

wherein R¹ and R² are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group;
c. purging the ALD reactor with an inert gas;
d. alternatively providing at least one of the aza-polysilane precursor, an oxygen-containing source and a nitrogen-containing source in the ALD reactor;
e. purging the ALD reactor with an inert gas; and wherein steps b through e are repeated under ALD process conditions until a desired thickness of the film is obtained
wherein the at least one aza-polysilane precursor comprises at least one member selected from the group consisting of 1,4-bis(cyclopentyl)-1,4-diaza-2,3,5,6-tetrasilacyclohexane, 1,4-bis(cyclohexyl)-1,4-diaza-2, 3,5,6-tetrasilacyclohexane, 1,4-bis(2,6-dimethylcyclohexyl)-1,4-Diaza-2,3,5,6-tetrasilacyclohexane, 1,4-bis(iso-propyl)-1,4-diaza-2,3,5,6-tetrasilacyclohexane, 1,4-bis(tert-butyl)-1,4-diaza-2,3,5,6-tetrasilacyclohexane, and 1,4-bis(tert-pentyl)-1,4-diaza-2,3,5,6-tetrasilacyclohexane; wherein the aza-polysilane precursor is prepared by reacting at least one of monochlorodisilane and monobromodisilane with a primary amine.

21. A method of forming a silicon-containing film via an atomic layer deposition (ALD) process, the method comprising the steps of:
   a. providing a substrate in an ALD reactor;
   b. providing in the ALD reactor at least one aza-polysilane precursor represented by the following Formula IB:

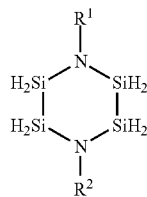

IB wherein $R^1$ and $R^2$ are independently selected from a linear or branched $C_1$ to $C_{10}$ alkyl group, a linear or branched $C_3$ to $C_{10}$ alkenyl group, a linear or branched $C_3$ to $C_{10}$ alkynyl group, $C_3$ to $C_{10}$ cyclic alkyl group, $C_3$ to $C_{10}$ hetero-cyclic alkyl group, a $C_5$ to $C_{10}$ aryl group, a $C_3$ to $C_{10}$ hetero-aryl group, a $C_2$ to $C_{10}$ dialkylamino group, and a $C_3$ to $C_{10}$ cyclic alkylamino group;

c. purging the ALD reactor with an inert gas;
   d. alternatively providing the aza-polysilane precursor, an oxygen-containing source and a nitrogen-containing source in the ALD reactor;
   e. purging the ALD reactor with an inert gas; and wherein steps b through e are repeated under ALD process conditions until a desired thickness of the film is obtained; and wherein the aza-polysilane precursor is prepared by reacting at least one of monochlorodisilane and monobromodisilane with a primary amine.

* * * * *